United States Patent
Choi et al.

(10) Patent No.: US 7,862,907 B2
(45) Date of Patent: Jan. 4, 2011

(54) DIMETHYLENECYCLOHEXANE COMPOUND, METHOD OF PREPARING THE SAME AND ORGANIC LIGHT EMITTING DEVICE COMPRISING THE SAME

(75) Inventors: Byoung-Ki Choi, Hwaseong-si (KR); Young-Hoon Kim, Uiwang-si (KR); Jong-Jin Park, Guri-si (KR); Myeong-Suk Kim, Suwon-si (KR); Sung-Hun Lee, Seoul (KR); Lyong-Sun Pu, Suwon-si (KR); Das Rupasree Ragini, Suwon-si (KR); Young-Hun Byun, Yongin-si (KR); Young-Mok Son, Hwaseong-si (KR); O-Hyun Kwon, Seoul (KR); Yi-Yeol Lyu, Yongin-si (KR)

(73) Assignee: Samsung Mobile Display Co., Ltd., Nongseo-Dong, Giheung-Gu, Yongin, Gyunggi-Do (KR)

( * ) Notice: Subject to any disclaimer, the term of this patent is extended or adjusted under 35 U.S.C. 154(b) by 1184 days.

(21) Appl. No.: 11/493,839

(22) Filed: Jul. 27, 2006

(65) Prior Publication Data

US 2007/0026258 A1    Feb. 1, 2007

(30) Foreign Application Priority Data

Jul. 28, 2005    (KR) .................. 10-2005-0069077

(51) Int. Cl.
*H01L 51/54* (2006.01)
*C09K 11/06* (2006.01)

(52) U.S. Cl. .............. 428/690; 428/917; 313/504; 313/506; 257/40; 257/E51.049; 257/E51.051; 564/427; 564/434; 585/26

(58) Field of Classification Search .............. None
See application file for complete search history.

(56) References Cited

U.S. PATENT DOCUMENTS

| 4,356,429 | A |   | 10/1982 | Tang |
| 5,759,444 | A | * | 6/1998 | Enokida et al. ........ 252/301.16 |
| 2001/0043043 | A1 |   | 11/2001 | Aoyama et al. |
| 2006/0068221 | A1 |   | 3/2006 | Saitoh et al. |
| 2007/0264526 | A1 |   | 11/2007 | Choi et al. |

FOREIGN PATENT DOCUMENTS

| JP | 11-003782 |   | 1/1999 |
| JP | 11-329734 |   | 11/1999 |
| JP | 2003186214 | A * | 7/2003 |
| JP | 2003270811 | A * | 9/2003 |
| JP | 2005-047811 |   | 2/2005 |

OTHER PUBLICATIONS

Machine translation of JP2003-186214. Date of publication: Jul. 3, 2003.*
Machine translation of JP2003-270811. Date of publication: Sep. 25, 2003.*
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tri(3-methylphenylphenyl-amino)triphenylamine (m-MTDATA), as Hole-Transport Materials", Adv. Mater. 1994, 6, No. 9, pp. 677-679.
Office Action (Paper No. 20091230) issued by U.S. PTO on Jan. 11, 2010 in U.S. Appl. No. 11/798,171.
Machine translation of JP2005-047811. Date of publication: Feb. 24, 2005.

* cited by examiner

*Primary Examiner*—Jennifer A Chriss
*Assistant Examiner*—Andrew K Bohaty
(74) *Attorney, Agent, or Firm*—Robert E. Bushnell, Esq.

(57) ABSTRACT

A dimethylenecyclohexane compound represented by formula 1, a method of preparing the same, and an organic light emitting device using the dimethylenecyclohexane are provided.

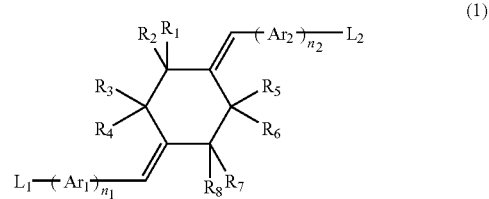

(1)

The dimethylenecyclohexane compound can improve the driving voltage, efficiency and color purity of the organic light emitting device.

20 Claims, 3 Drawing Sheets

DIMETHYLENECYCLOHEXANE COMPOUND, METHOD OF PREPARING THE SAME AND ORGANIC LIGHT EMITTING DEVICE COMPRISING THE SAME

CROSS-REFERENCE TO RELATED PATENT APPLICATION AND CLAIM OF PRIORITY

This application claims the benefit of Korean Patent Application No. 10-2005-0069077, filed on 28 Jul., 2005, in the Korean Intellectual Property Office, the disclosure of which is incorporated herein in its entirety by reference.

BACKGROUND OF THE INVENTION

1. Field of the Invention

The present invention relates to a dimethylenecyclohexane compound, a method of preparing the same, and an organic light emitting device using the dimethylenecyclohexane, and more particularly, to a dimethylenecyclohexane compound which has excellent electrical properties, thermal stability and photochemical stability such that an organic light emitting device using the dimethylenecyclohexane compound has a low driving voltage, and excellent efficiency and color purity, a method of preparing the same, and an organic light emitting device including an organic layer formed of the dimethylenecyclohexane compound.

2. Description of the Related Art

Light emitting devices, which are self-emitting devices, have wide viewing angles, excellent contrast, and quick response. Examples of light emitting devices include inorganic light emitting devices, which include emitting layers formed of an inorganic compound, and organic light emitting devices, which include emitting layers formed of an organic compound. Organic light emitting devices are brighter, and have a lower operating voltage and quicker response compared to inorganic light emitting devices. Furthermore, organic light emitting devices can realize multi colors. Due to these advantages of organic light emitting devices, much research into organic light emitting devices has been carried out.

Typically, an organic light emitting device has an anode/organic emissive layer/cathode structure. An organic light emitting device can also have various other structures, such as an anode/hole injection layer/hole transport layer/emissive layer/electron transport layer/electron injection layer/cathode structure or an anode/hole injection layer/hole transport layer/emissive layer/hole blocking layer/electron transport layer/electron injection layer/cathode structure.

A material that is used to form the emissive layer or the hole injection layer can be, for example, an anthracene substituted by two naphthyl groups disclosed in Japanese Patent Laid-Open Publication No. 1999-003782. However, the driving voltage, efficiency and color purity of an organic light emitting device using the conventional compound do not meet desired levels. Accordingly, a material having improved properties must be developed.

SUMMARY OF THE INVENTION

The present invention provides a dimethylenecyclohexane compound that can improve the driving voltage, efficiency and color purity of an organic light emitting device, a method of preparing the same, and an organic light emitting device using the dimethylenecyclohexane compound.

According to an aspect of the present invention, there is provided a dimethylenecyclohexane compound represented by formula 1 below:

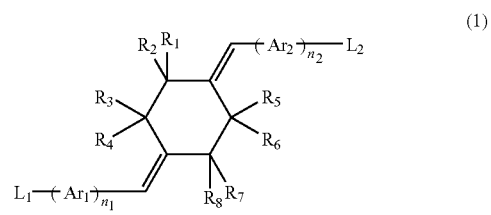

(1)

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z''), and Z' and Z'' are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group;

each $Ar_1$ is each independently a substituted or unsubstituted $C_6$-$C_{30}$ arylene group, or a substituted or unsubstituted $C_2$-$C_{30}$ heteroarylene group;

each $Ar_2$ is each independently a substituted or unsubstituted $C_6$-$C_{30}$ arylene group, or a substituted or unsubstituted $C_2$-$C_{30}$ heteroarylene group; and $n_1$ and $n_2$ are each independently integers from 1 to 5; and $L_1$ and $L_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group having —N(R')(R''), and the R' and R'' are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

According to another aspect of the present invention, there is provided a method of preparing a dimethylenecyclohexane compound represented by formula 1, the method including: reacting compounds represented by formula 1a with compounds represented by formulae 1b and 1c to obtain a compound represented by formula 1d; and reacting the compound represented by formula 1d with compounds represented by compounds represented by formulae $L_1$-$Q_1$ and $L_2$-$Q_2$ to obtain the compound represented by formula 1:

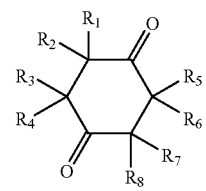

(1a)

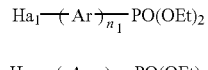

(1b)

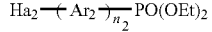

(1c)

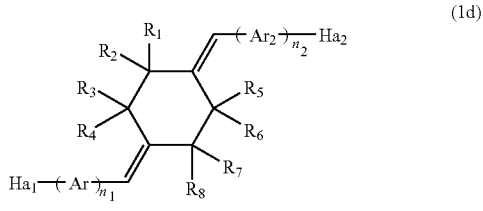

(1d)

where $R_1, R_2, R_3, R_4, R_5, R_6, R_7, R_8, Ar_1, Ar_2, n_1, n_2, L_1$ and $L_2$ are already described above;

$Ha_1$ and $Ha_2$ are halogen; and $Q_1$ and $Q_2$ are B-containing groups or are H when $L_1$ and $L_2$ are substituted amino groups having —N(R')(R'').

According to another aspect of the present invention, there is provided an organic light emitting device including a first electrode; a second electrode; and at least one organic layer which is formed of the dimethylenecyclohexane compound described above and interposed between the first electrode and the second electrode.

The organic light emitting device using the dimethylenecyclohexane compound of the present invention exhibits low driving voltage, improved efficiency, and color purity due to its excellent thermal stability, photochemical stability and optical properties.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

Figure 1A:
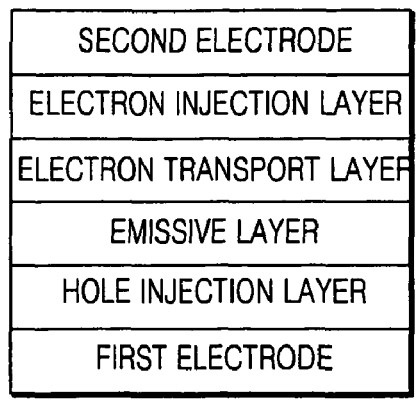
FIGS. 1A through 1C are schematic sectional view of organic light emitting devices according to embodiments of the present invention.

Hereinafter, the present invention will be described more fully with reference to the accompanying drawings, in which exemplary embodiments of the invention are shown.

A dimethylenecyclohexane compound according to an embodiment of the present invention is represented by formula 1 below:

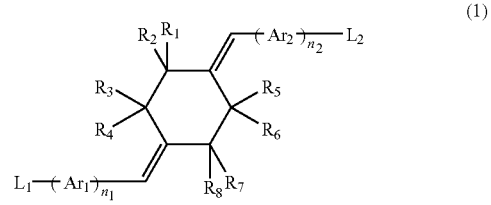

(1)

where the two double bonds and the cyclohexane group connected to the two double bonds increase the solubility of the compound represented by formula 1 and the $—(Ar_1)_{n1}-L_1$ and $—(Ar_2)_{n2}-L_2$ improve the film proccessibility, quantum yield, thermal stability, photo chemical stability and photoluminescence (PL) properties of the compound represented by formula 1. Accordingly, the dimethylenecyclohexane compound represented by formula 1 is suitable for a material forming an organic layer interposed between first and second electrodes in organic light emitting devices. The dimethylenecyclohexane compound represented by formula 1 is suitable for an organic layer, preferably, a hole injection layer, a hole transport layer or an emissive layer.

In formula 1, $R_1, R_2, R_3, R_4, R_5, R_6, R_7$ and $R_8$ may each independently be a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z''). Z' and Z'' are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group.

When the alkyl group, the alkoxy group, the aryl group, the heteroaryl group, the cycloalkyl group or the heterocycloalkyl group is substituted, the substituents may independently include at least one of —F; —Cl; —Br; —CN; —NO$_2$; —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

In formula 1, $Ar_1$ and $Ar_2$ may each independently be a substituted or unsubstituted $C_6$-$C_{30}$ arylene group, or a substituted or unsubstituted $C_2$-$C_{30}$ heteroarylene group.

The arylene group is a bivalent group having at least one aromatic ring, and also includes a bivalent group having two or more arylene groups which are bound to or fused with each other. The heteroarylene group is a bivalent group having at least one aromatic ring substituted with at least one substituent such as N, O, S and P in at least one carbon atom of the arylene groups.

When the arylene group or the heteroarylene group is substituted, the substituents may independently include at least one of —F; —Cl; —Br; —CN; —NO$_2$; —OH; a C$_1$-C$_{20}$ alkyl group that is unsubstituted or substituted with —F, —Cl, —Br, —CN, —NO$_2$ or —OH; a C$_1$-C$_{20}$ alkoxy group that is unsubstituted or substituted with —F, —Cl, —Br, —CN, —NO$_2$ or —OH; a C$_6$-C$_{30}$ aryl group that is unsubstituted or substituted with a C$_1$-C$_{20}$ alkyl group, a C$_1$-C$_{20}$ alkoxy group, —F, —Cl, —Br, —CN, —NO$_2$ or —OH; a C$_2$-C$_{30}$ heteroaryl group that is unsubstituted or substituted with a C$_1$-C$_{20}$ alkyl group, a C$_1$-C$_{20}$ alkoxy group, —F, —Cl, —Br, —CN, —NO$_2$ or —OH; a C$_5$-C$_{20}$ cycloalkyl group that is unsubstituted or substituted with a C$_1$-C$_{20}$alkyl group, a C$_1$-C$_{20}$alkoxy group, —F, —Cl, —Br, —CN, —NO$_2$ or —OH; and a C$_5$-C$_{30}$ heterocycloalkyl group that is unsubstituted or substituted with a C$_1$-C$_{20}$ alkyl group, a C$_1$-C$_{20}$ alkoxy group, —F, —Cl, —Br, —CN, —NO$_2$ or —OH.

Preferably, in formula 1, Ar$_1$ and Ar$_2$ may each independently be one of a phenylene group, a C$_1$-C$_{10}$ alkylphenylene group, a C$_1$-C$_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (a,a-dimethylbenzen)phenylene group, a (N,N'-dimethyl)aminophenylene group, a (N,N'-diphenyl)aminophenylene group, a (C$_1$-C$_{10}$ alkylcyclohexyl)phenylene group, a (anthracenyl)phenylene group, a pentalenylene group, an indenylene group, a naphthylene group, a C$_1$-C$_{10}$ alkylnaphthylene group, a C$_1$-C$_{10}$ alkoxynaphthylene group, a halonaphthylene group, a cyanonaphthylene group, a biphenylenylene group, a C$_1$-C$_{10}$ alkyl biphenylenylene group, a C$_1$-C$_{10}$ alkoxy biphenylenylene group, an anthracenylene group, an azulenylene group, a heptalenylene group, an acenaphthylenylene group, a phenalenylene group, a fluorenylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a C$_{1-10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, and a thianthrenylene group. However, Ar$_1$ and Ar$_2$ are not limited to these groups.

Among the above examples, Arm and Ar$_2$ may be, for example, a phenylene group or an anthracenylene group.

Ar$_1$ and Ar$_2$ can be different or identical, and preferably identical.

In formula 1, n$_1$ and n$_2$ are respectively the number of —Ar$_1$— and Ar$_2$—. n$_1$ and n$_2$ may each independently be integers from 1 to 5, preferably, from 1 to 3.

When n$_1$ is 2 or greater, the Ar$_1$s can be identical or different and when n$_2$ is 2 or greater, the Ar$_2$s can be identical or different.

In formula 1, L$_1$ and L$_2$ may each independently be a substituted or unsubstituted C$_6$-C$_{30}$ aryl group, a substituted or unsubstituted C$_2$-C$_{30}$ heteroaryl group, a substituted or unsubstituted C$_5$-C$_{20}$ cycloalkyl group, a substituted or unsubstituted C$_5$-C$_{30}$ heterocycloalkyl group, or a substituted amino group having —N(R')(R''), and the R' and R'' may each independently be a hydrogen, a substituted or unsubstituted C$_1$-C$_{20}$ alkyl group, a substituted or unsubstituted C$_6$-C$_{30}$ aryl group, a substituted or unsubstituted C$_2$-C$_{30}$ heteroaryl group, a substituted or unsubstituted C$_5$-C$_{20}$ cycloalkyl group, or a substituted or unsubstituted C$_5$-C$_{30}$ heterocycloalkyl group.

The aryl group is a monovalent group having at least one aromatic ring, and also includes a monovalent group having two or more aromatic rings which are bound to or fused with each other. The heteroaryl group is a group having at least one aromatic ring substituted with at least one substituent, such as N, O, S and P in at least one carbon atom of the aryl groups. The cycloalkyl group is an alkyl group being a ring, and the heterocycloalkyl group is a group substituted with at least one substituent such as N, O, S and P in at least one carbon atom of the cycloalkyl group.

When the aryl group, the heteroaryl group, the cycloalkyl group and the heterocycloalkyl group are substituted, the substituents may independently include at least one of —F; —Cl; —Br; —CN; —NO$_2$; —OH; a C$_1$-C$_{20}$ alkyl group that is unsubstituted or substituted with —F, —Cl, —Br, —CN, —NO$_2$ or —OH; a C$_1$-C$_{20}$ alkoxy group that is unsubstituted or substituted with —F, —Cl, —Br, —CN, —NO$_2$ or —OH; a C$_6$-C$_{30}$ aryl group that is unsubstituted or substituted with a C$_1$-C$_{20}$ alkyl group, a C$_1$-C$_{20}$ alkoxy group, —F, —Cl, —Br, —CN, —NO$_2$ or —OH; a C$_2$-C$_{30}$ heteroaryl group that is unsubstituted or substituted with a C$_1$-C$_{20}$ alkyl group, a C$_1$-C$_{20}$ alkoxy group, —F, —Cl, —Br, —CN, —NO$_2$ or —OH; a C$_5$-C$_{20}$ cycloalkyl group that is unsubstituted or substituted with a C$_1$-C$_{20}$ alkyl group, a C$_1$-C$_{20}$ alkoxy group, —F, —Cl, —Br, —CN, —NO$_2$ or —OH; and a C$_5$-C$_{30}$ heterocycloalkyl group that is unsubstituted or substituted with a C$_1$-C$_{20}$alkyl group, a C$_1$-C$_{20}$ alkoxy group, —F, —Cl, —Br, —CN, —NO$_2$ or —OH.

Preferably, in formula 1, L$_1$ and L$_2$ may each independently be one of a phenyl group, a C$_1$-C$_{10}$ alkylphenyl group, a C$_1$-C$_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (a,a-dimethylbenzen)phenyl group, a (N,N'-dimethyl)aminophenyl group, a (N,N'-diphenyl)aminophenyl group, a (C$_1$-C$_{10}$ alkylcyclohexyl)phenyl group, a biphenyl group, a C$_1$-C$_{10}$ alkylbiphenyl group, a C$_1$-C$_{10}$ alkoxybiphenyl group, a pentalenyl group, an indenyl group, a naphthyl group, a C$_1$-C$_{10}$ alkylnaphthyl group, a C$_1$-C$_{10}$ alkoxynaphthyl group, a halonaphthyl group, a cyanonaphthyl group, a biphenylenyl group, a C$_1$-C$_{10}$ alkyl biphenylenyl group, a C$_1$-C$_{10}$ alkoxy biphenylenyl group, an anthracenyl group, C$_1$-C$_{10}$ alkyl anthracenyl group, a C$_1$-C$_{10}$ alkoxy anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a C$_{1-10}$alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, a $C_1$-$C_{10}$ alkylcyclohexyl group, a $C_1$-$C_{10}$ alkoxycyclohexyl group, an oxiranyl group, a pyrrolidinyl group, a pyrazolidinyl group, an imidazolidinyl group, a piperidinyl group, a piperazinyl group, a morpholinyl group and an amino group having —N(R')(R"). However, $L_1$ and $L_2$ are not limited to these groups.

In formula 1, R' and R" may each independently be one of a hydrogen, a phenyl group, a $C_1$-$C_{10}$ alkyl phenyl group, a $C_1$-$C_{10}$alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (a,a-dimethylbenzen)phenyl group, a (N,N'-dimethyl)aminophenyl group, a (N,N'-diphenyl)aminophenyl group, a ($C_1$-$C_{10}$ alkylcyclohexyl)phenyl group, an anthracenyl phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group and a $C_1$-$C_{10}$ alkyl biphenylenyl group. However, R' and R" are not limited to these groups.

Among the above groups, it is preferred that $L_1$ and $L_2$ may each independently be one of a phenyl group, a naphthyl group, an anthracenyl group, and N(R')(R") that R' and R" are each independently a naphthyl group or a phenyl group.

More particularly, the dimethylenecyclohexane compound according to an embodiment of the present invention may be represented by one of the following compounds of formulae 2 through 15, but is not limited thereto.

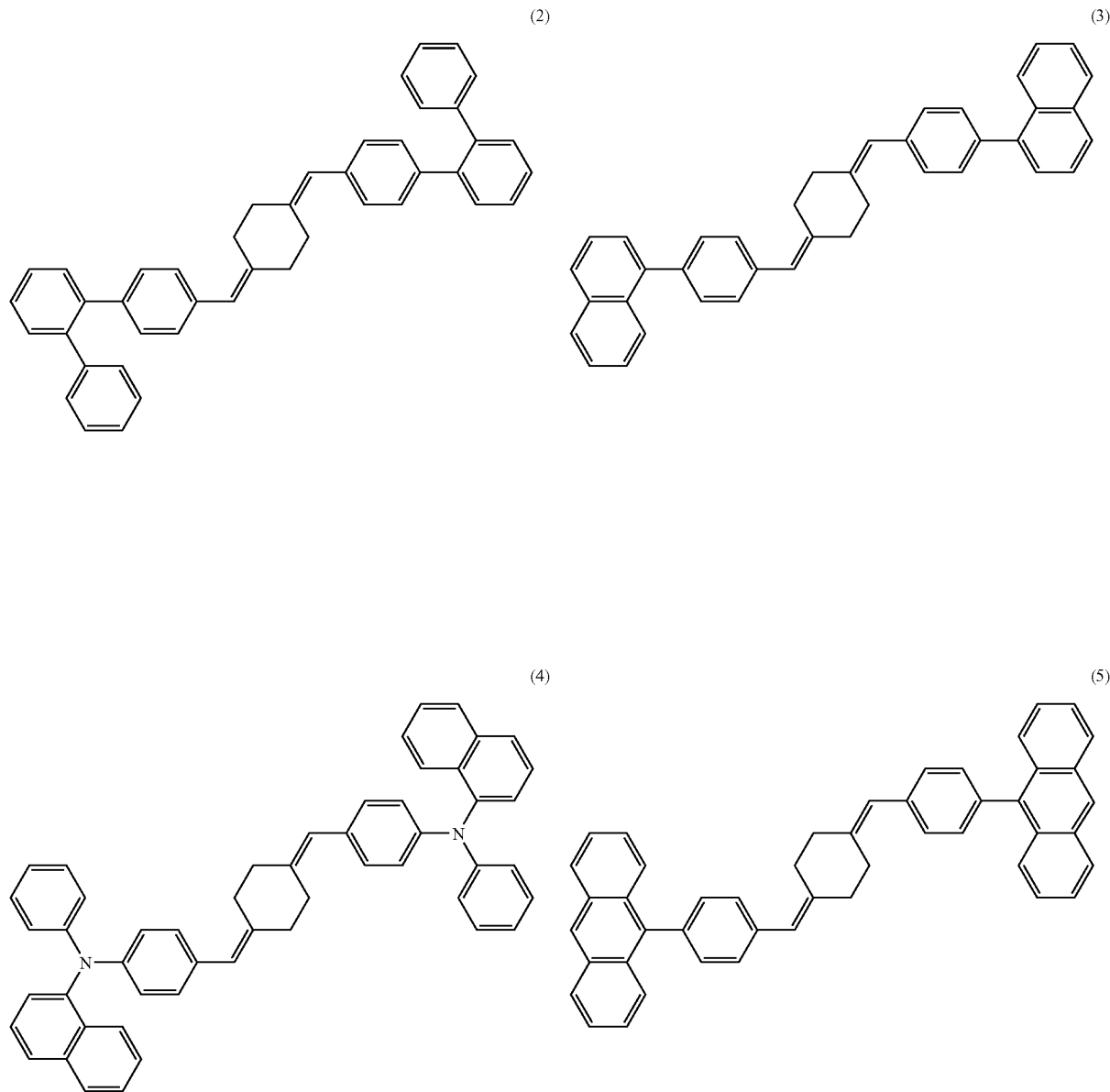

(6)
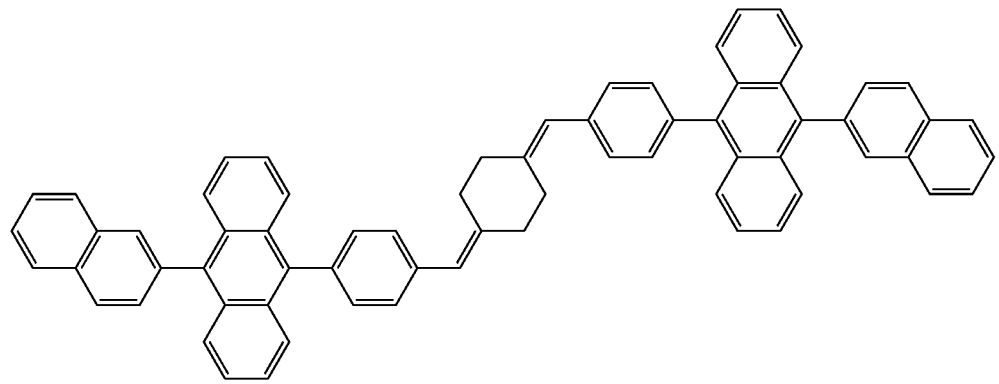
(7)
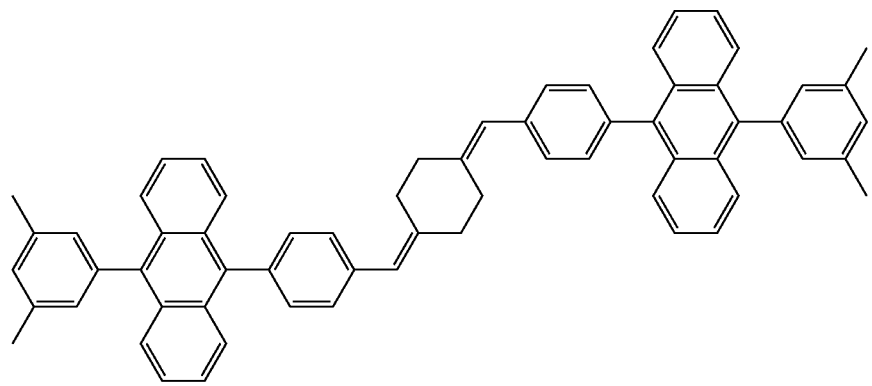
(8)
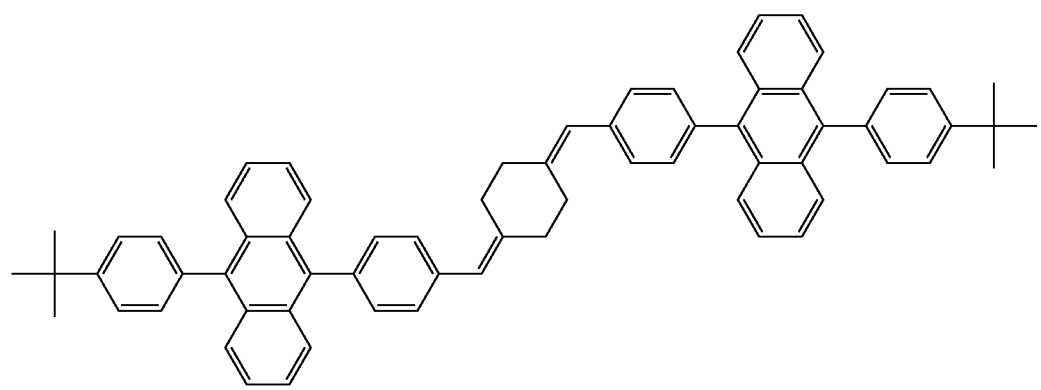
(9)
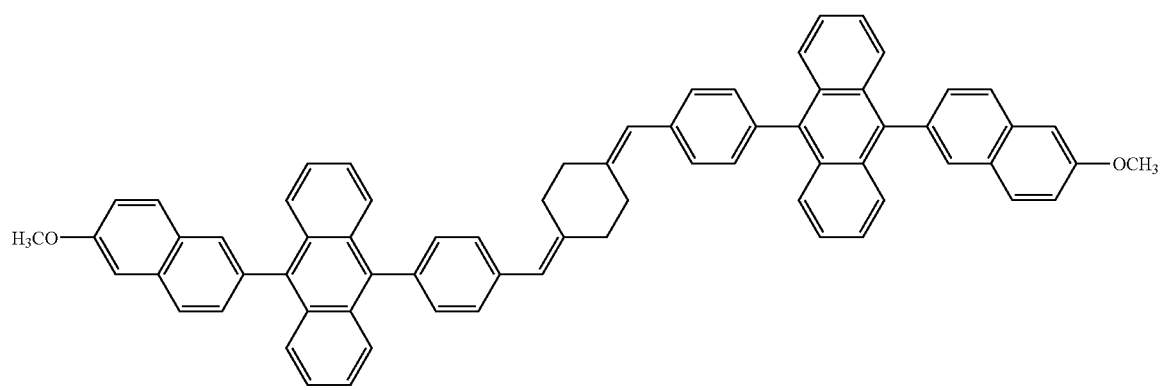

-continued
(10)
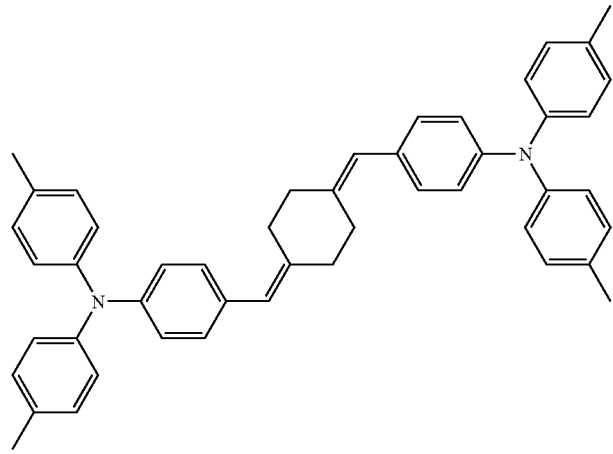
(11)
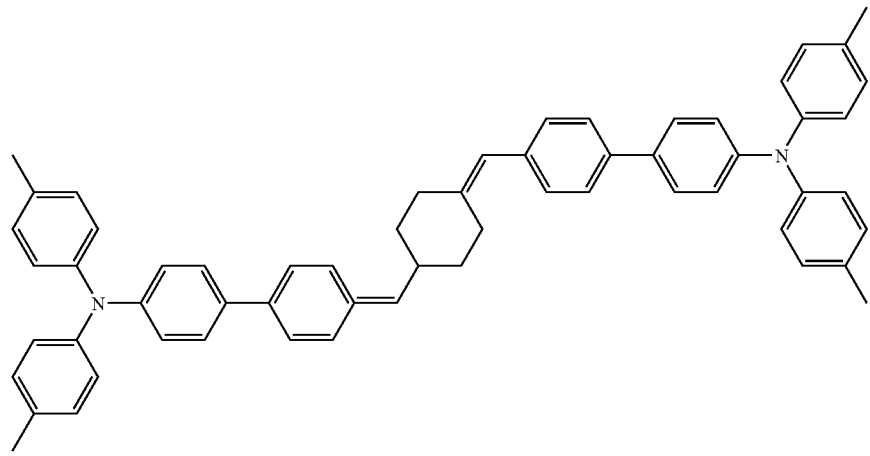
(12)
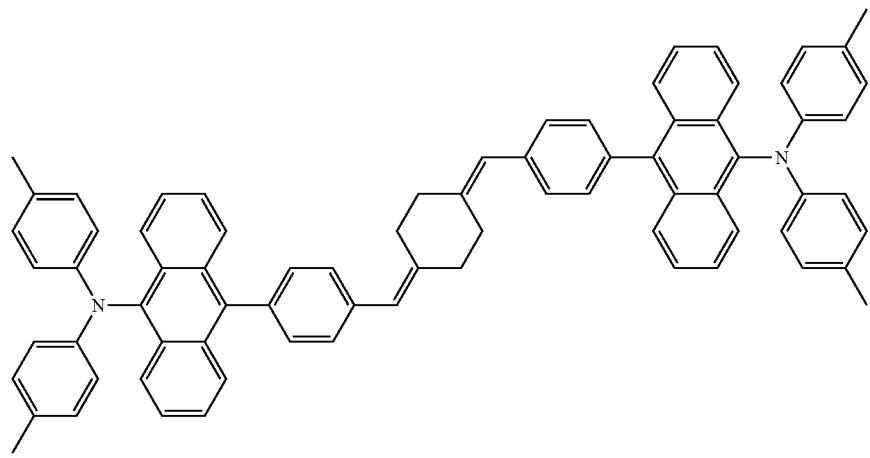

-continued
(13)
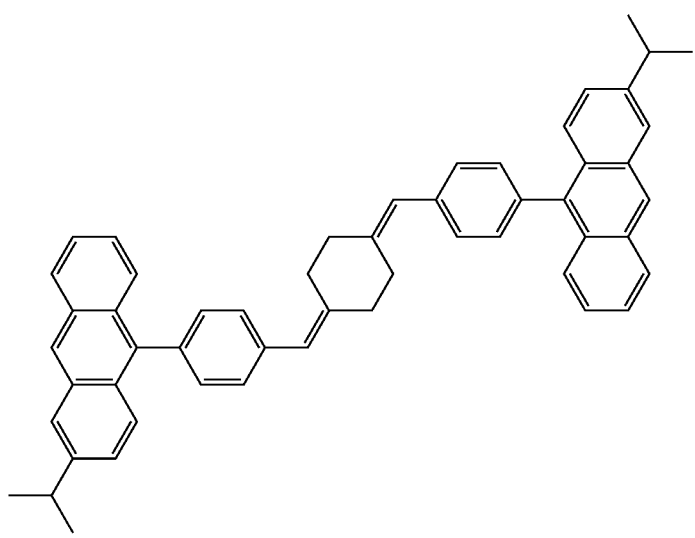
(14)
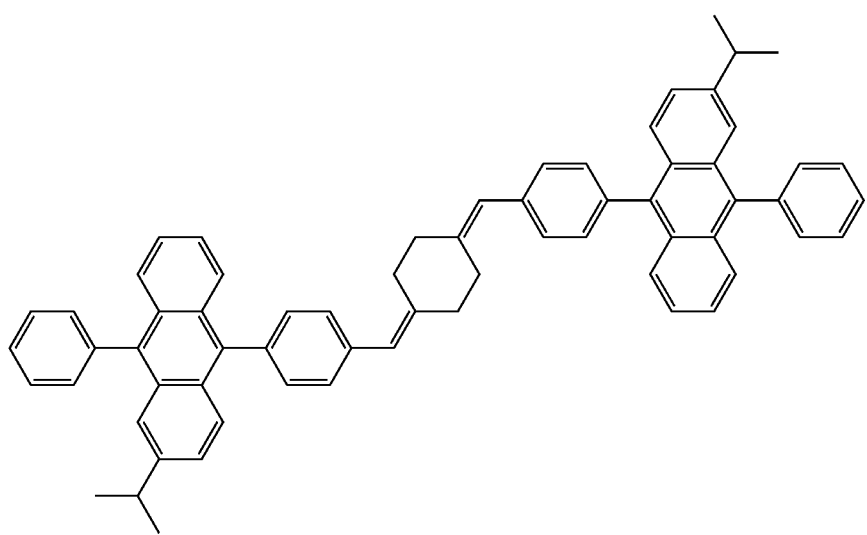
(15)
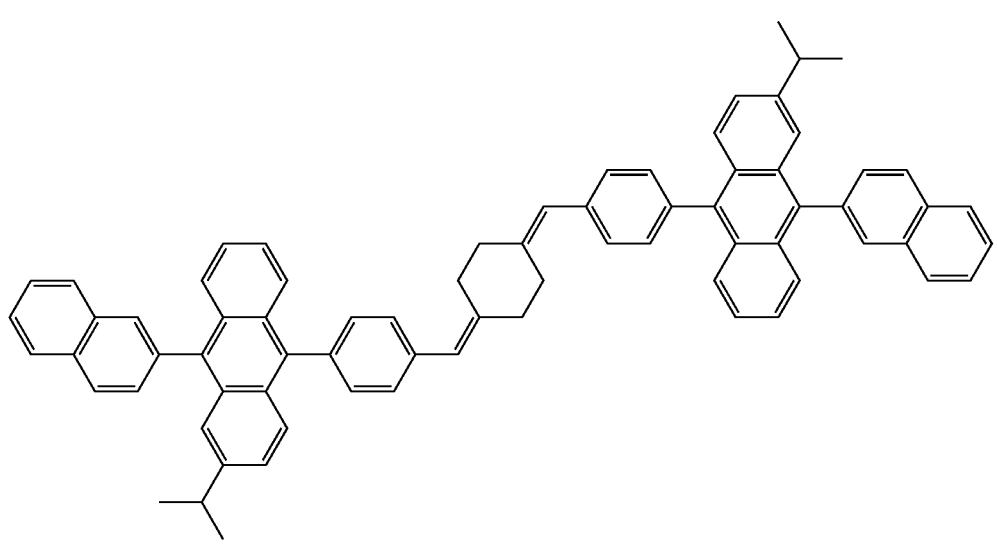

The dimethylenecyclohexane compound represented by formula 1 can be synthesized using a conventional organic synthesis principle. A method of preparing the dimethylenecyclohexane compound according to an embodiment of the present invention includes reacting compounds represented by formula 1a with compounds represented by formulae 1b and 1c to obtain a compound represented by formula 1d, and reacting the compound represented by formula 1d with compounds represented by formulae $L_1$-$Q_1$ and $L_2$-$Q_2$ to obtain the compound represented by formula 1:

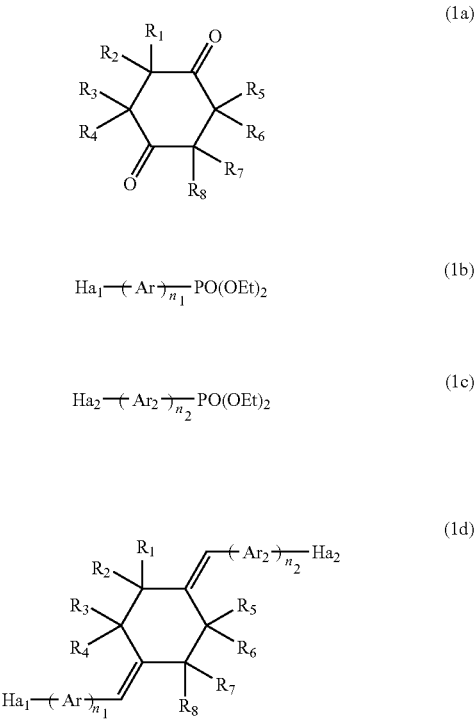

where $R_1, R_2, R_3, R_4, R_5, R_6, R_7, R_8, Ar_1, Ar_2, n_1, n_2, L_1$ and $L_2$ are as described above.

In formulae 1b and 1c, $Ha_1$ and $Ha_2$ are each independently a halogen such as F, Cl, Br or I. For example, $Ha_1$ and $Ha_2$ can both be Br.

$L_1$ and $L_2$ are as described above.

$Q_1$ and $Q_2$ are each a B-containing group. Alternatively, $Q_1$ and $Q_2$ are H when $L_1$ and $L_2$ are substituted amino groups having —N(R')(R").

Examples of the B-containing group include

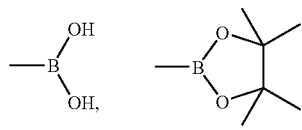

and the like, but the B-containing group is not limited thereto.

Reaction Scheme 1 below illustrates a detailed mechanism for synthesizing the dimethylenecyclohexane compound according to an embodiment of the present invention.

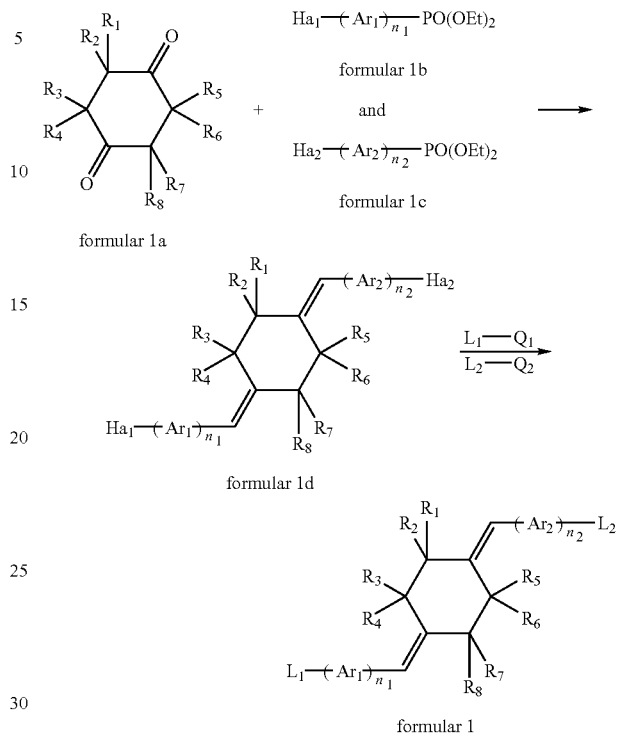

First, the compound represented by formula 1a is reacted with the compounds represented by formulae 1b and 1c to obtain the compound represented by formula 1d. The compound represented by formula 1a can be a commercially available compound and the compounds represented by formulae 1b and 1c can be obtained by reacting triethyl phosphite (P(OEt)$_3$) with an aryl compound substituted with methyl halide (for example, by reacting triethyl phosphite with bromobenzylbromide). However, methods of preparing the compounds are not limited thereto. Subsequently, the compound represented by formula 1d is reacted with compounds represented by formulae $L_1$-$Q_1$ and $L_2$-$Q_2$ to obtain the compound represented by formula 1. This reaction can be performed, for example, in the presence of $K_2CO_3$ and Pd(PPh$_3$)$_4$(tetrakis(triphenylphosphine)palladium). Compounds represented by formulae $L_1$-$Q_1$ and $L_2$-$Q_2$ can be boronic acids having $L_1$ and $L_2$ groups or dioxaborolanes having $L_1$ and $L_2$ groups, or amines having $L_1$ and $L_2$ groups, but are not limited thereto. The structures of all of the resulting compounds can be identified using 1H NMR and Mass Spectrometer.

In the method of preparing the dimethylenecyclohexane compound, $Ar_1$ and $Ar_2$ can be identical, $n_1$ and $n_2$ can be identical, $Ha_1$ and $Ha_2$ can be identical and $L_1$ and $L_2$ can be identical.

The dimethylenecyclohexane compound according to the above-described embodiment can be used in an organic light emitting device. An organic light emitting device according to an embodiment of the present invention includes a first electrode, a second electrode, and at least one organic layer interposed between the first electrode and the second electrode. The organic layer can be formed of the dimethylenecyclohexane compound represented by formula 1 described above. In detail, the organic layer can be a hole injection layer, a hole transport layer, or an emissive layer.

The organic layer may have various structures. In other words, at least one of a hole injection layer, a hole transport layer, a hole blocking layer, an electron blocking layer, an electron transport layer, and an electron injection layer can be formed between the first electrode and the second electrode.

Figure 1B:
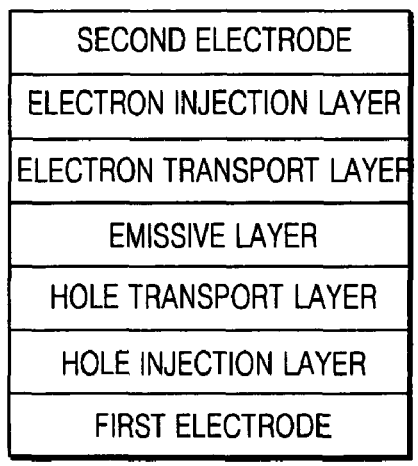
Figure 1C:
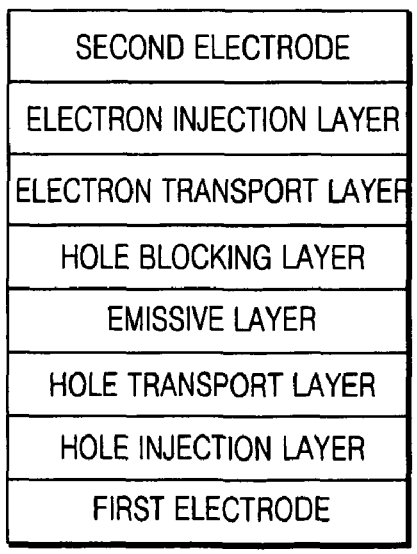

The exemplary organic light emitting devices according to embodiments of the present invention are schematically illustrated in FIGS. 1A, 1B, and 1C. In FIG. 1A, the organic light emitting device has a first electrode/hole injection layer/emissive layer/electron transport layer/electron injection layer/second electrode structure. In FIG. 1B, the organic light emitting device has a first electrode/hole injection layer/hole transport layer/emissive layer/electron transport layer/electron injection layer/second electrode structure. In FIG. 1C, the organic light emitting device has a first electrode/hole injection layer/hole transport layer/emissive layer/hole blocking layer/electron transport layer/electron injection layer/second electrode structure. At least one of the hole injection layer, the hole transport layer and the emissive layer may include the dimethylenecyclohexane compound represented by formula 1.

The emissive layer of the organic light emitting device according to an embodiment of the present invention may include a red, green, blue or white phosphorescent or fluorescent dopant. The phosphorescent dopant can be an organic metal compound which contains at least one of Ir, Pt, Os, Ti, Zr, Hf, Eu, Tb, and Tm.

Hereinafter, a method of manufacturing an organic light emitting device according to an embodiment of the present invention will be described with reference to the organic light emitting device illustrated in FIG. 1C.

First, a first electrode is formed by depositing or sputtering a high work-function material on a substrate. The first electrode can be an anode. The substrate, which can be any substrate that is used in conventional organic light emitting devices, may be a glass substrate or a transparent plastic substrate that has excellent mechanical strength, thermal stability, transparency, and surface smoothness, is easily treated, and is waterproof. The first electrode can be formed of ITO, IZO, $SnO_2$, ZnO, or any transparent material which has high conductivity.

Then, a hole injection layer (HIL) can be formed on the first electrode by vacuum deposition, spin coating, casting, Langmuir Blodgett (LB), or the like.

When the HIL is formed by vacuum deposition, vacuum deposition conditions may vary according to the compound that is used to form the HIL, and the desired structure and thermal properties of the HIL to be formed. In general, however, the vacuum deposition may be performed at a deposition temperature of 100° C.-500° C., under a pressure of $10^{-8}$ torr-$10^{-3}$ torr, at a deposition speed of 0.01-100 Å/sec, and to a layer thickness of 10 Å-5 μm.

When the HIL is formed by spin coating, coating conditions may vary according to a compound that is used to form the HIL, and the desired structure and thermal properties of the HIL to be formed. In general, however, the coating speed may be in the range of about 2000 rpm to 5000 rpm, and a temperature for heat treatment, which is performed to remove a solvent after coating, may be in the range of about 80° C. to 200° C.

The HIL can be formed of the dimethylenecyclohexane compound represented by formula 1 described above. Alternatively, the material may be a phthalocyanine compound, such as copper phthalocyanine disclosed in U.S. Pat. No. 4,356,429, which is incorporated herein by reference; a starburst type amine derivative, such as TCTA, m-MTDATA, and m-MTDAPB, disclosed in Advanced Material, 6, p. 677 (1994) which is incorporated herein by reference; soluble and conductive polymer such as polyaniline/Dodecylbenzenesulfonic acid (Pani/DBSA); poly(3,4-ethylened ioxythiophene)/Poly(4-styrenesulfonate (PEDOT/PSS): polyaniline/camphor sulfonic acid (Pani/CSA); (polyaniline)/poly (4-styrenesulfonate) (PANI/PSS); or the like.

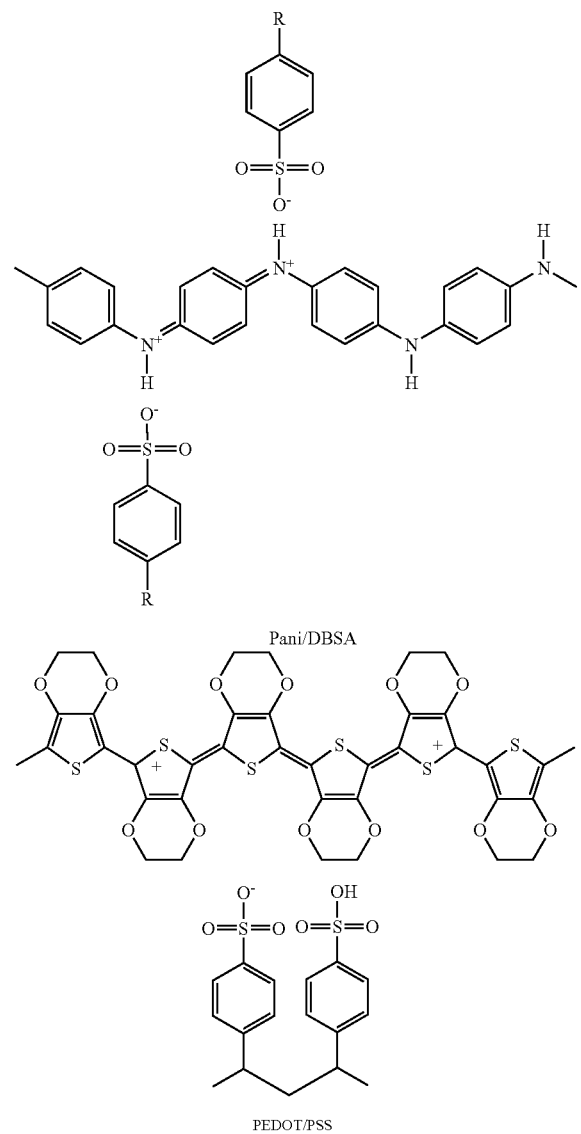

Pani/DBSA

PEDOT/PSS

The thickness of the HIL may be in the range of about 100 Å to 10000 Å, and preferably, in the range of 100 Å to 1000 Å. When the thickness of the HIL is less than 100 Å, the hole injecting ability of the HIL may be reduced. On the other hand, when the thickness of the HIL is greater than 10000 Å, a driving voltage of the device can be increased.

Then, a hole transport layer (HTL) can be formed on the HIL using a vacuum deposition method, a spin coating method, a casting method, Langmuir Blodgett (LB), or the like. When the HTL is formed by vacuum deposition or spin coating, the conditions for deposition and coating are similar to those for the formation of the HIL, although conditions for the deposition and coating may vary according to the material that is used to form the HTL.

The HTL can be formed of the dimethylenecyclohexane compound represented by formula 1 described above. The HTL may be formed of any material that is conventionally used to form an HTL. For example, the HTL can be formed of a carbazole derivative, such as N-phenylcarbazole, polyvinylcarbazole; a typical amine derivative having an aromatic condensation ring such as N,N'-bis(3-methylphenyl)-N,N'-diphenyl-[1,1-biphenyl]-4,4'-diamine (TPD), N,N'-di(naphthalene-1-yl)-N,N'-diphenyl benzidine (a-NPD); or the like.

The thickness of the HTL may be in the range of about 50 Å to about 1000 Å, and preferably, 100 Å to about 600 Å. When the thickness of the HTL is less than 50 Å, a hole transporting ability of the HTL may be reduced. On the other hand, when the thickness of the HTL is greater than 1000 Å, the driving voltage of the device may increase.

Then, an emissive layer (EML) can be formed on the HTL by vacuum deposition, spin coating, casting, LB, or the like. When the EML is formed by vacuum deposition or spin coating, the conditions for deposition and coating are similar to those for the formation of the HIL, although the conditions for deposition and coating may vary according to the material that is used to form the EML.

The EML may be formed of the dimethylenecyclohexane compound represented by formula 1 according to an embodiment of the present invention. In this case, a proper host material or dopant that is known in the art can be used together with the dimethylenecyclohexane compound represented by formula 1, or the dimethylenecyclohexane compound represented by formula 1 can be used by itself. The host material may be, for example, $Alq_3$, 4,4'-N,N'-dicarbazole-biphenyl (CBP), or poly(n-vinylcarbazole) (PVK). As for the dopant material, examples of a fluorescent dopant include IDE102 and IDE105 obtained from Idemitsu Co., C545T obtained from Hayashibara Co., and the like, and examples of a phosphorescent dopant include a red phosphorescent dopant PtOEP, RD 61 obtained from UDC Co., a green phosphorescent dopant $Ir(PPy)_3$ (PPy=2-phenylpyridine), a blue phosphorescent dopant F2Irpic, and the like. The structure of DPAVBi represented by formula 16 used as a dopant is shown below:

The concentration of the dopant is not limited, but is conventionally in the range of 0.01 to 15 parts by weight based on 100 parts by weight of a host.

The thickness of the EML may be in the range of about 100 Å to 1000 Å, and preferably, in the range of 200 Å to 600 Å. When the thickness of the EML is less than 100 Å, the emissive ability of the EML may be reduced. On the other hand, when the thickness of the EML is greater than 1000 Å, the driving voltage of the device may increase.

A hole blocking layer (HBL) can be formed on the HTL using a vacuum deposition method, a spin coating method, a casting method, Langmuir Blodgett (LB), or the like, to prevent diffusion of triplet excitons or holes into an electron transport layer when the phosphorescent dopant is used to form the EML. When the HBL is formed by vacuum deposition or spin coating, the conditions for deposition and coating are similar to those for the formation of the HIL, although the conditions for deposition and coating may vary according to the material that is used to form the HBL. The HBL may be formed of, for example, an oxadiazole derivative, a triazole derivative, a phenanthroline derivative, or a hole blocking material disclosed in JP No. 11-329734(A1), or 2,9-dimethyl-4,7-diphenyl-1,10-phenanthroline (BCP).

The thickness of the HBL may be in the range of about 50 Å to 1000 Å, and preferably, in the range of 100 Å to 300 Å. When the thickness of the HBL is less than 50 Å, the hole blocking ability of the HBL may be reduced. On the other hand, when the thickness of the HBL is greater than 1000 Å, the driving voltage of the device may increase.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a quinoline derivative which stably transports injected electrons from a cathode, in particular, tris(8-quinolinorate)aluminum ($Alq_3$), TAZ, Balq or the like, which is known in the art.

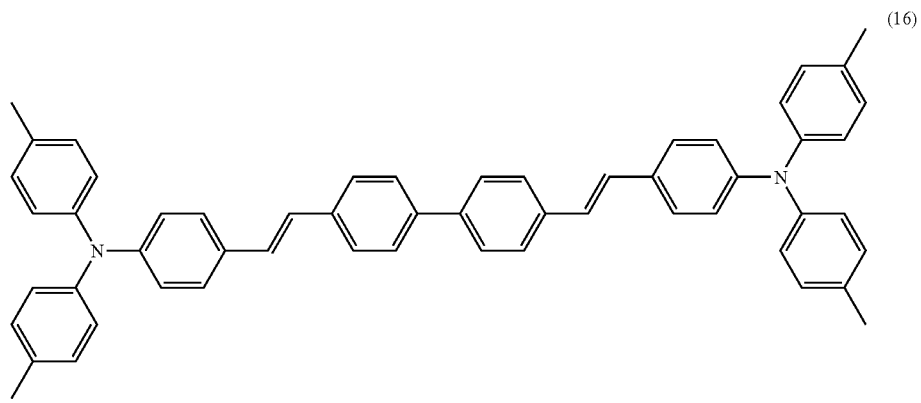

(16)

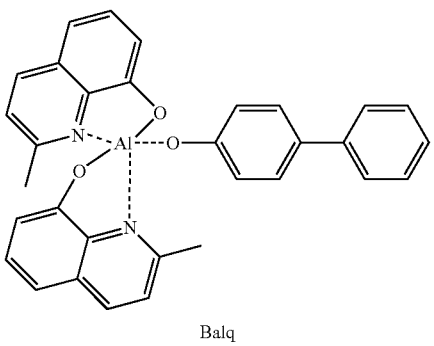

Balq

The thickness of the ETL may be in the range of about 100 Å to 1000 Å, and preferably, 200 Å to 500 Å. When the thickness of the ETL is less than 100 Å, the electron transporting ability of the ETL may be reduced. On the other hand, when the thickness of the ETL is greater than 1000 Å, the driving voltage of the device may increase.

Then, an electron injection layer (EIL), which is formed of a material allowing easy injection of electrons from a cathode, can be formed on the ETL. The material that is used to form the EIL is not limited.

The EIL may be formed of LiF, NaCl, CsF, $Li_2O$, BaO, or the like, which is known in the art. Conditions for the deposition of the EIL are, in general, similar to conditions for the formation of the HIL, although they may vary according to the material that is used to form the EIL.

The thickness of the EIL may be in the range of about 1 Å to 100 Å, and preferably, 5 Å to 50 Å. When the thickness of the EIL is less than 1 Å, the electron injecting ability of the EIL may be reduced. On the other hand, when the thickness of the EIL is greater than 100 Å, the driving voltage of the device may increase.

Finally, a second electrode can be formed on the EIL by vacuum deposition, sputtering, or the like. The second electrode can be used as a cathode. The second electrode may be formed of a low work-function metal, an alloy, an electrically conductive compound, or a combination of these. For example, the second electrode may be formed of Li, Mg, Al, Al—Li, Ca, Mg—In, Mg—Ag, or the like. Alternatively, a transparent cathode formed of ITO or IZO can be used to produce a front surface light emitting device.

The organic light emitting device according to an embodiment of the present invention may have the first electrode/HIL/HTL/EML/HBL/ETL/EIL/second electrode structure illustrated in FIG. 1C. However, the structure of the organic light emitting device according to embodiments of the present invention may vary (for example, the structure of the organic light emitting device illustrated in FIG. 1A, which will be described in greater detail in Examples below.)

Hereinafter, Synthesis Examples and Examples of Compounds respectively represented by formulae 2 through 12 according to embodiments of the present invention (hereinafter, respectively referred to as "Compound 2" through "Compound 12") will be described in detail. However, the Examples are provided to facilitate the understanding of the present invention only, are not intended to limit the scope of the present invention.

EXAMPLES

Synthesis Example 1

Compound 2 was synthesized through Reaction Scheme 2 below:

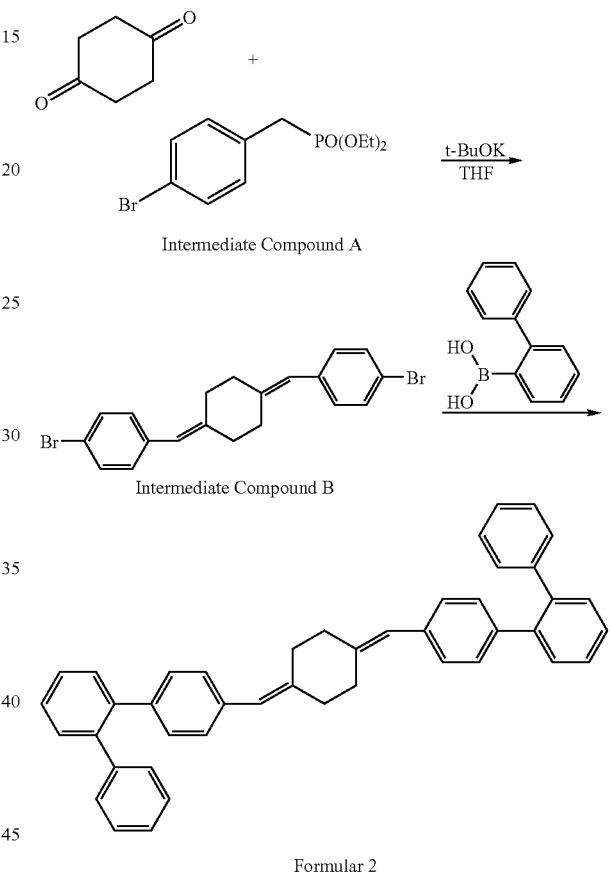

Formular 2

Synthesis of Intermediate Compound A 10 g (40 mmol) of 4-bromobenzyl bromide was mixed with 13.3 g (80 mmol) of triethylphosphite [$P(OCH_2CH_3)_3$] and stirred at 185° C. for 6 hours. The solvent was removed under decreased pressure and the result was cooled to room temperature to obtain 11.8 g of a white solid powder (96%).

$^1$H-NMR ($CDCl_3$, 300 MHz, ppm): 7.42 (d, 2H), 7.18 (d, 2H), 4.02 (m, 4H), 3.12 (s, 1H), 3.05 (s, 1H), 1.25 (t, 6H).

Synthesis of Intermediate Compound B 12.5 g (110 mmol) of t-BuOK was added to 31.6 g (100 mmol) of Intermediate Compound A dissolved in 300 ml of tetrahydrofuran (THF) and reacted at 50° C. for one hour. 5 g (40 mmol) of 1,4-cyclohexadion was added to the mixture and reacted at 70° C. for one day. After 20 ml of ethanol was added to the mixture and dried in a vacuum, 200 ml of methylene chloride was added to the dried mixture. An organic layer collected from the mixture was washed twice with 200 ml of water and dried over anhydrous magnesium sulfate to evaporate the solvent. The dried result was purified using silica gel column chromatography to obtain 9.7 g of Intermediate Compound B (Yield 58%).

$^1$H-NMR (CDCl$_3$, 300 MHz, ppm): 7.42 (d, 4H), 7.10 (d, 4H), 6.25 (s, 2H), 2.53-2.31 (m, 8H).

Synthesis of Compound 2

11.8 g (60 mmol) of 4-biphenylyl boronic acid, 1.4 g (1.0 mmol) of tetrakis (triphenylphosphine) palladium and 9.9 g (72 mmol) of K$_2$CO$_3$ dissolved in 100 ml of toluene and 10 ml of water were added to 10 g (24 mmol) of Intermediate Compound B dissolved in 200 ml of THF and stirred at a reflux temperature for 24 hours. The reaction mixture was cooled to room temperature and 100 ml of diethylether was added thereto. The mixture was washed twice with 50 ml of water. An organic layer was collected from the washed result and dried over anhydrous magnesium sulfate to evaporate the solvent. As a result, a crude product was obtained. The crude product was purified using silica gel column chromatography and recrystallized to obtain 6.1 g of Compound 2 (Yield 45%).

Synthesis Example 2

Compound 3 was synthesized through Reaction Scheme 3 below:

Reaction Scheme 3

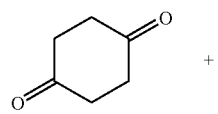

+

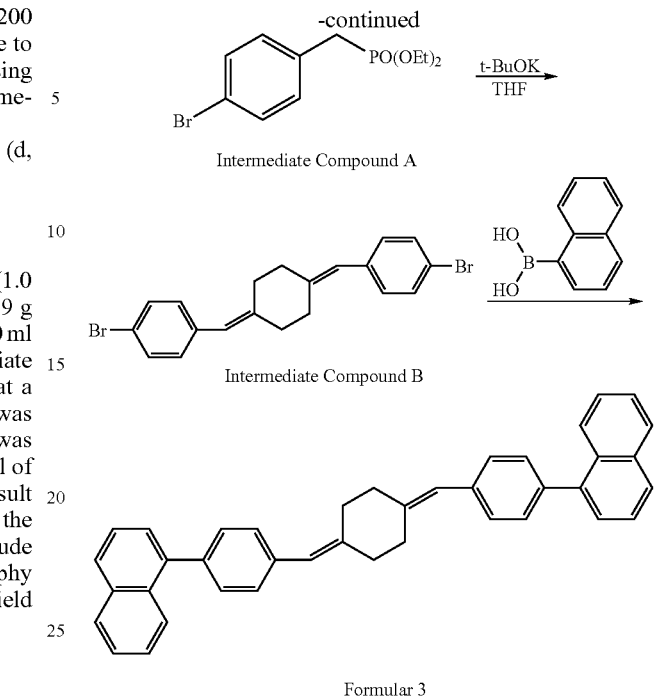

Compound 3 was obtained in the same manner as Compound 2 was obtained in Synthesis Example 1, except that 1-naphthalene boronic acid was used instead of 4-biphenylyl boronic acid.

Synthesis Example 3

Compound 4 was synthesized through Reaction Scheme 4 below:

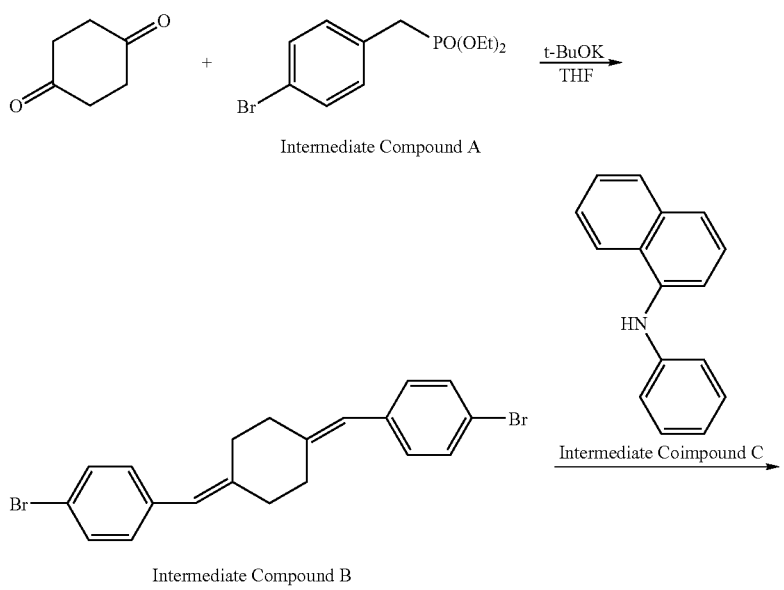

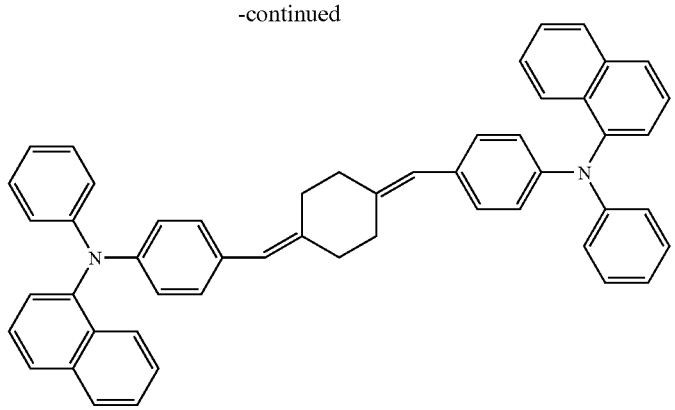

Formulat 4

2.94 g (14.9 mmol) of N-phenyl-1-naphthylamine (Intermediate Compound C), 0.5 g (0.54 mmol) of tris(dibenzylideneacetone)dipalladium ($Pd_2(dba)_3$), 0.083 g (0.41 mmol) of t-butylphosphine, and 2.88 g (30 mmol) of NaO-t-Bu were added to 4.45 g (10.6 mmol) of Intermediate Compound B dissolved in 80 ml of o-xylene and stirred at room temperature for 4 hours. 100 ml of dichloromethane was added to the reaction mixture and the result was washed twice with 100 ml of water. An organic layer was collected from the washed result and dried over anhydrous magnesium sulfate to evaporate the solvent. As a result, a crude product was obtained. The crude product was purified using silica gel column chromatography and recrystallized to obtain 3.2 g of Compound 4 (Yield 47%).

$^1$H-NMR ($CDCl_3$, 300 MHz, ppm): 7.95 (m, 2H), 7.80 (d, 1H), 7.49-7.34 (m, 4H), 7.23-7.18 (m, 2H), 7.10-6.94 (m, 7H), 6.23 (s, 1H), 6.23 (s, 1H), 2.59-2.31 (m, 4H)

Synthesis Example 4

Compound 5 was synthesized through the Reaction Scheme 5 below:

Reaction Scheme 5

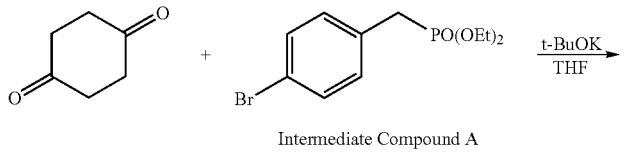

Intermediate Compound A

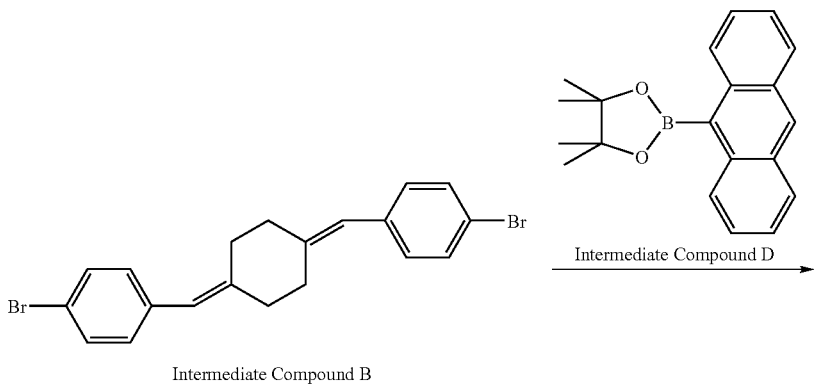

Intermediate Compound B

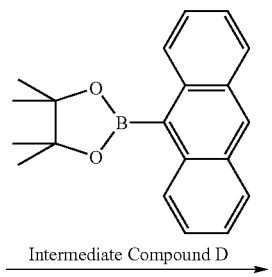

Intermediate Compound D

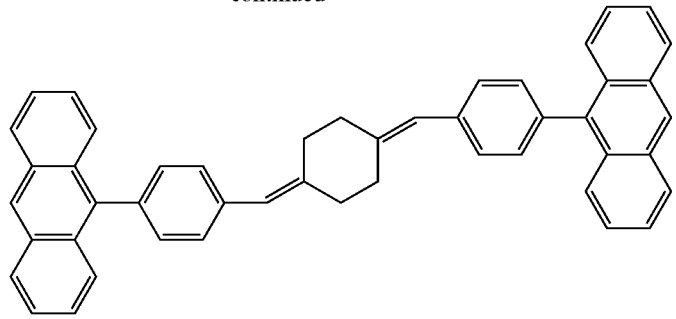

Formulatt 5

Compound 5 was obtained in the same manner as Compound 2 was obtained in Synthesis Example 1 except that Intermediate Compound D was used instead of 4-biphenyly boronic acid. Intermediate Compound D was synthesized through Reaction Scheme 5' below:

$^1$H-NMR (CDCl$_3$, 300 MHz, ppm): 8.50 (s, 2H), 8.07 (d, 4H), 7.76 (d, 4H), 7.50-7.25 (m, 16H), 6.53 (s, 2H), 2.84 (m, 4H), 2.58 (m, 4H)

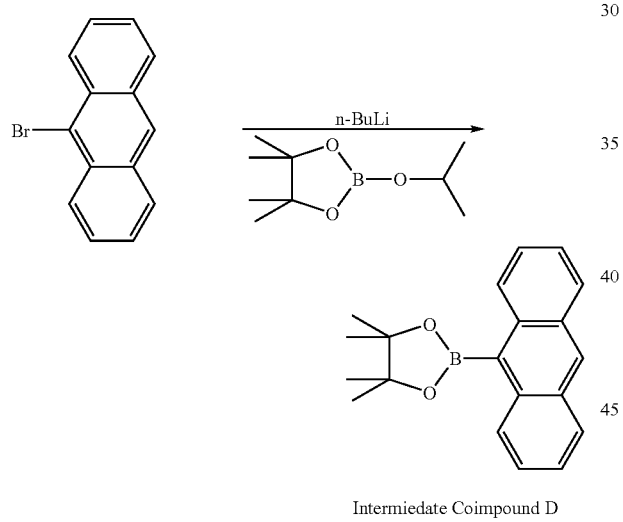

Reaction Scheme 5'

Intermiedate Coimpound D 3.2 ml (8.0 mmol) of 2.5 M n-butyl lithium was slowly added to 1.03 g (4.0 mmol) of 9-bromo anthracenes dissolved in 100 ml of THF at −78° C. and reacted at −78° C. for one hour. 1.49 g (8.0 mmol) of 2-isopropoxy-4,4,5,5-tetramethyl-1,3,2-dioxaborolane was added to the mixture and reacted at −78° C. for 3 hours, stirred at room temperature for 12 hours and methanol was then added to the reaction mixture. 100 ml of methylene chloride was added to the reaction mixture and the result was washed twice with 50 ml of water. An organic layer was collected from the washed result and dried over anhydrous magnesium sulfate to evaporate the solvent. As a result, a crude product was obtained. The crude product was purified using silica gel column chromatography to obtain 0.67 g of Intermediate Compound D (Yield 55%).

$^1$H-NMR (CDCl$_3$, 300 MHz, ppm): 8.45 (m, 3H), 7.99 (d, 2H), 7.48 (m, 4H), 1.58 (m, 4H)

Synthesis Example 5

Compound 6 was synthesized through the Reaction Scheme 6 below:

Reaction Scheme 6

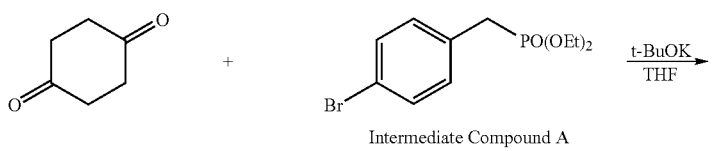

Intermediate Compound A

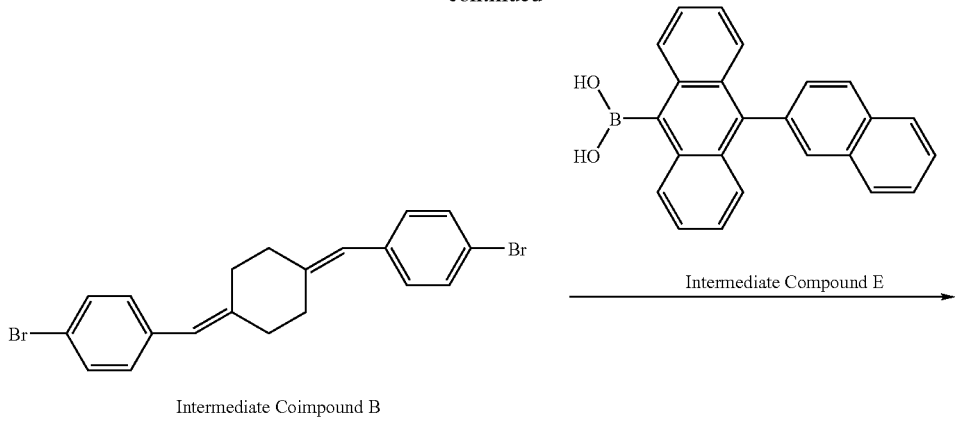

Intermediate Coimpound B

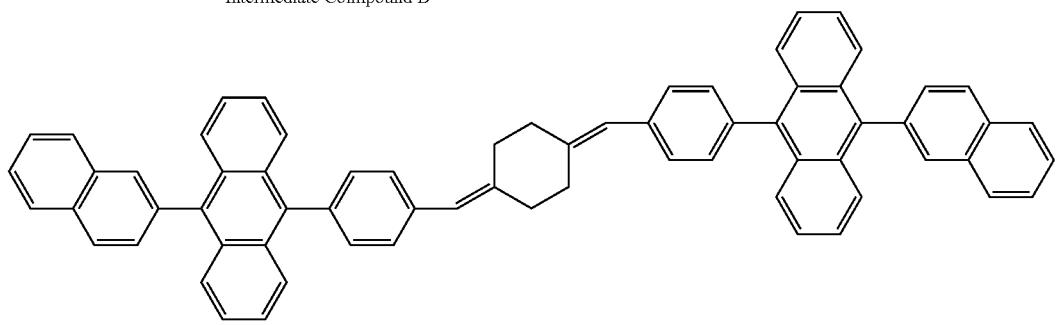

Formular 6

Compound 6 was obtained in the same manner as Compound 2 was obtained in Synthesis Example 1, except that Intermediate Compound E was used instead of 4-biphenylene boronic acid. Intermediate Compound E was synthesized through Reaction Scheme 6' below:

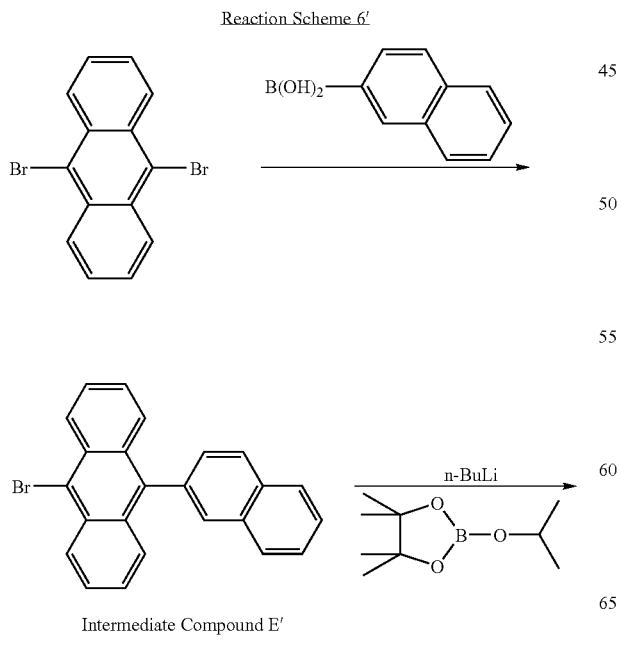

Intermediate Compound E'

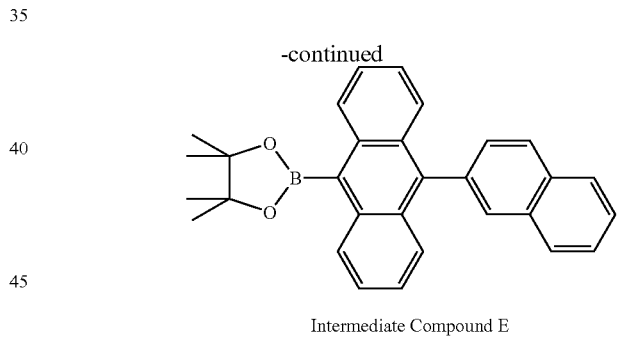

Intermediate Compound E 5.6 g (32.7 mmol) of 1-naphthalene boronic acid was added to 11.0 g (32.7 mmol) of 9,10-dibromo anthracene dissolved in 300 ml of THF and 1.9 g (1.6 mmol) of tetrakis(triphenylphosphine) palladium and 4.5 g (32.7 mmol) of $K_2CO_3$ dissolved in 300 ml of toluene and 50 ml of water were added to the reaction mixture and stirred at a reflux temperature for 24 hours. The solvent was evaporated and 100 ml of chloroform was added to the reaction mixture. The mixture was washed twice with 100 ml of water. An organic layer was collected from the washed mixture and dried over anhydrous magnesium sulfate to evaporate the solvent. As a result, a crude product was obtained. The crude product was purified using silica gel column chromatography and recrystallized to produce 8.2 g of Intermediate Compound E' (Yield 65%).

$^1$H-NMR (CDCl$_3$, 300 MHz, ppm) 8.47 (d, 2H), 8.02 (m, 2H), 7.88 (d, 2H), 7.66-7.45 (m, 7H), 7.45 (m, 2H), 1.62 (s, 12H).

8 ml (20 mmol) of 2.5 M n-butyl lithium was added to 3.8 g (10 mmol) of Intermediate Compound E' at −78° C. and stirred for one hour. 3.72 g (20 mmol) of 2-isopropoxy-4,4,5,5-tetramethyl-1,3,2-dioxaborolane was added to the reaction mixture and stirred at −78° C. for 2 hours and at room temperature for 18 hours, and the solvent was evaporated. 100 ml of methylene chloride was added to the reaction mixture and the result was washed twice with 50 ml of water. An organic layer was collected from the washed result and dried over anhydrous magnesium sulfate to evaporate the solvent. As a result, a crude product was obtained. The crude product was purified using silica gel column chromatography and recrystallized to produce 2.7 g of Intermediate Compound E (Yield 62%).

Synthesis Example 6

Compound 7 was synthesized through Reaction Scheme 7 below:

Reaction Scheme 7

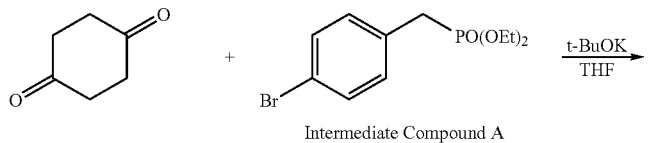

Intermediate Compound A

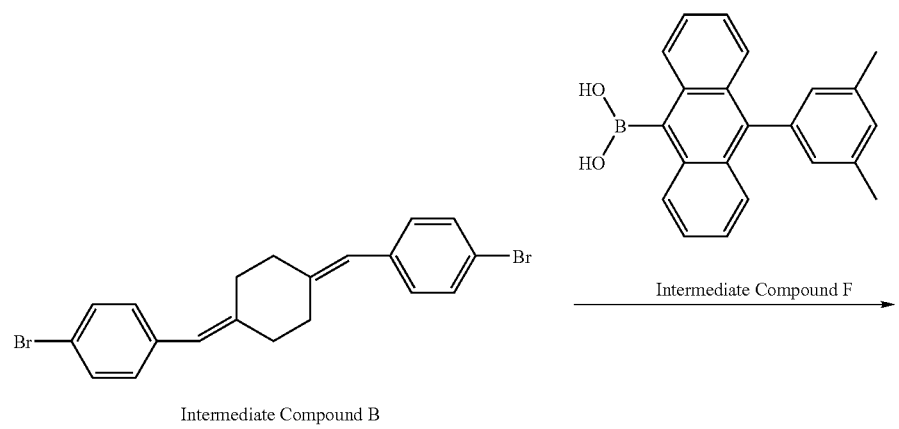

Intermediate Compound B

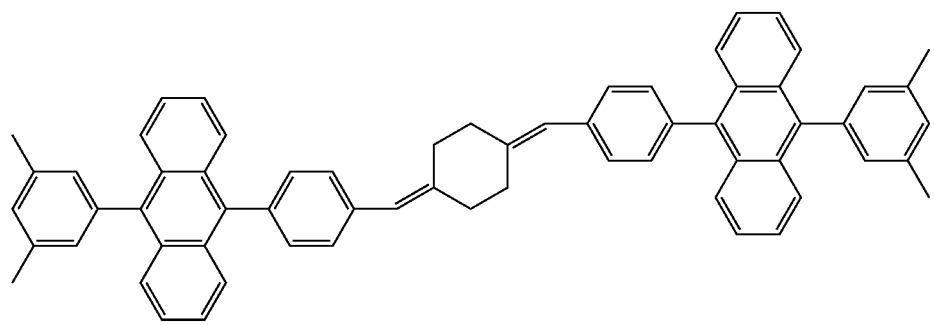

Formular 7

Compound 7 was obtained in the same manner as Compound 2 was obtained in Synthesis Example 1, except that Intermediate Compound F was used instead of 4-biphenylene boronic acid. Intermediate Compound F was synthesized in the same manner as Intermediate Compound E was prepared through Reaction Scheme 6' in Synthesis Example 5 except that 2,4-dimethyl phenyl boronic acid was used instead of 1-naphtalene boronic acid.

Synthesis Example 7

Compound 8 was synthesized through Reaction Scheme 8 below:

Reaction Scheme 8

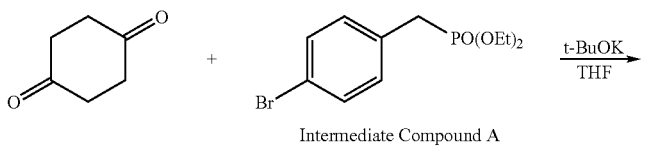

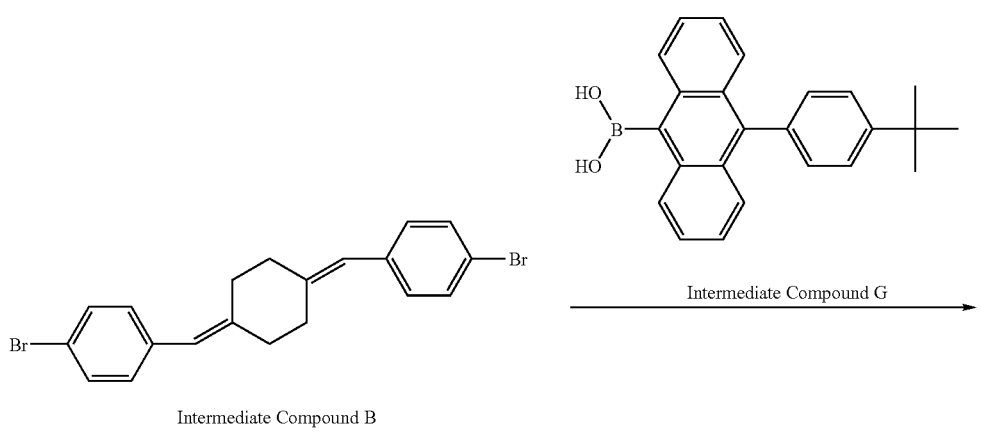

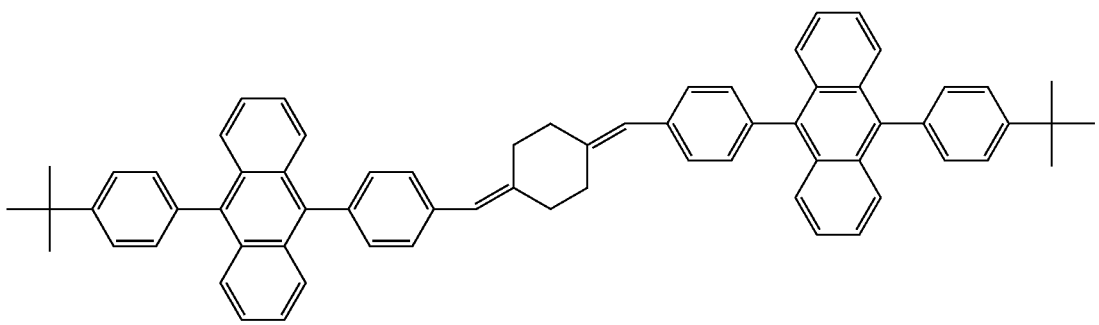

Formular 8

Compound 8 was obtained in the same manner as Compound 2 was prepared in Synthesis Example 1 except that Intermediate Compound G was used instead of 4-biphenylene boronic acid. Intermediate G was synthesized in the same manner as Intermediate Compound E was prepared through Reaction Scheme 6' in Synthesis Example 5 except that 4-tert-butylphenyl boronic acid was used instead of 1-naphthalene boronic.

Synthesis Example 8

Compound 9 was synthesized through Reaction Scheme 9 below:

Reaction Scheme 9

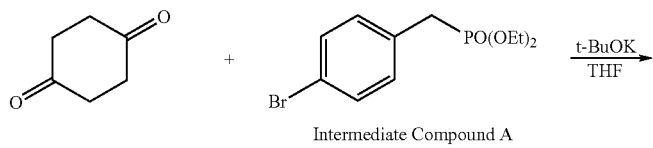

Intermediate Compound A

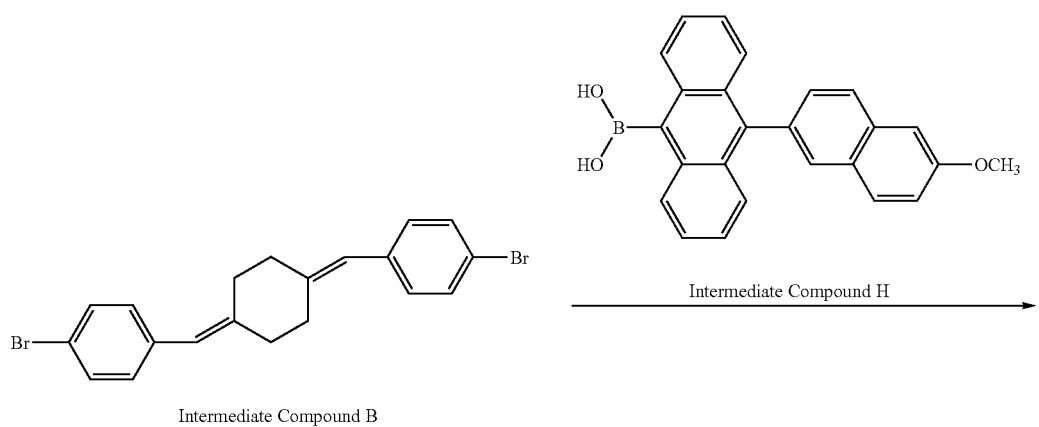

Intermediate Compound B

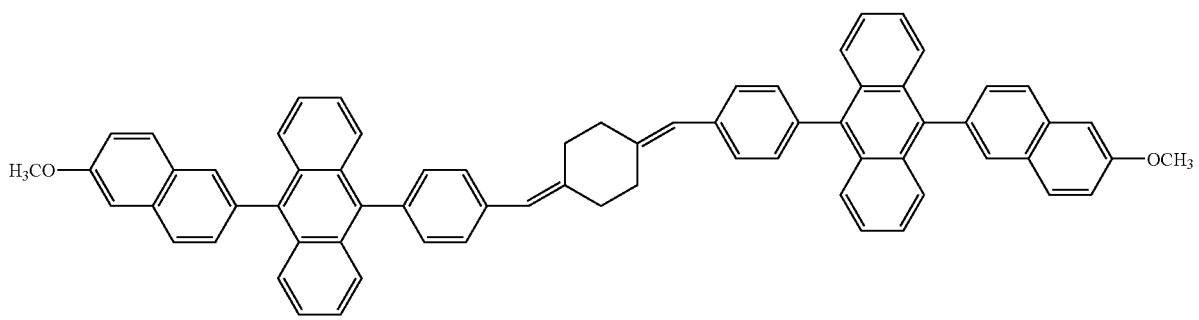

Formular 9

Compound 9 was obtained in the same manner as Compound 2 was prepared in Synthesis Example 1 except that Intermediate Compound H was used instead of 4-biphenylene boronic acid. Intermediate H was synthesized in the same manner as Intermediate Compound E was prepared through Reaction Scheme 6' in Synthesis Example 5 except that 2-methoxy naphthalene boronic acid was used instead of 1-naphtalene boronic acid.

Synthesis Example 9

Compound 10 was synthesized through Reaction Scheme 10 below:

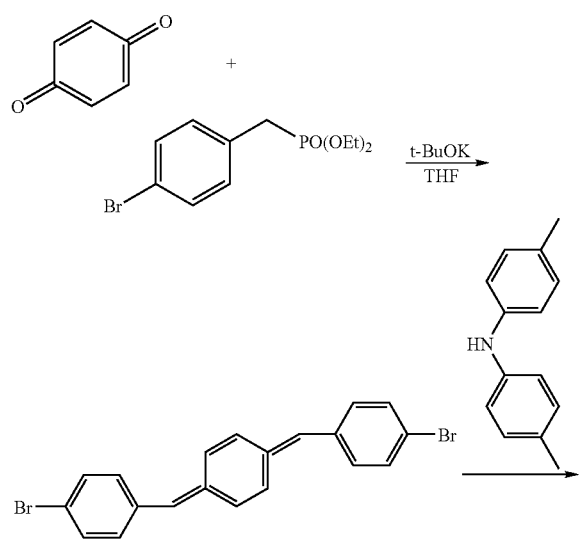

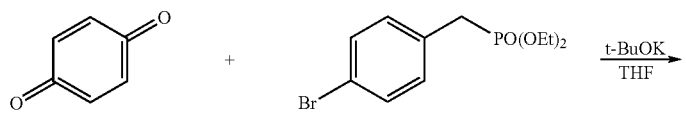

Formular 10

Compound 10 was obtained in the same manner as Compound 4 was prepared in Synthesis Example 3 except that ditolylamine was used instead of N-phenyl-1-naphthylamine.

Synthesis Example 10

Compound 11 was synthesized through Reaction Scheme 11 below:

Reaction Scheme 11

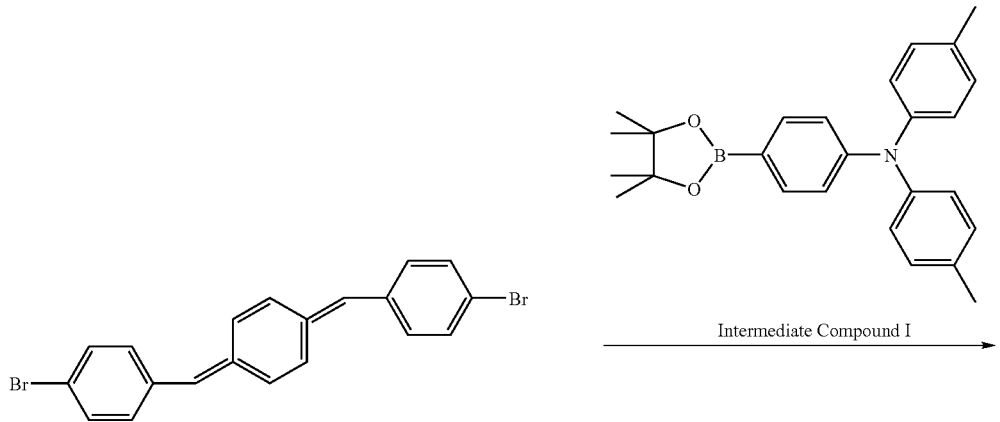

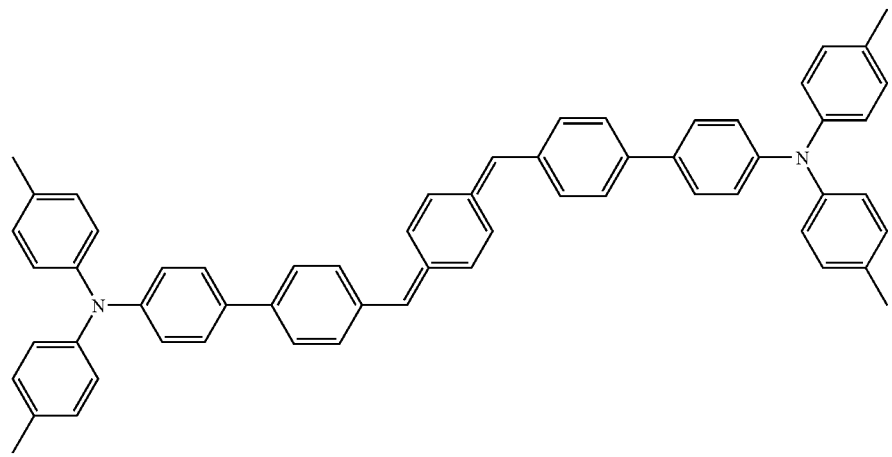

Formular 11

Compound 11 was produced in the same manner as Compound 2 was prepared in Synthesis Example 1 except that Intermediate Compound I was used instead of 4-biphenylene boronic acid. Intermediate Compound I was synthesized through Reaction Scheme 11' below:

Reaction Scheme 11'

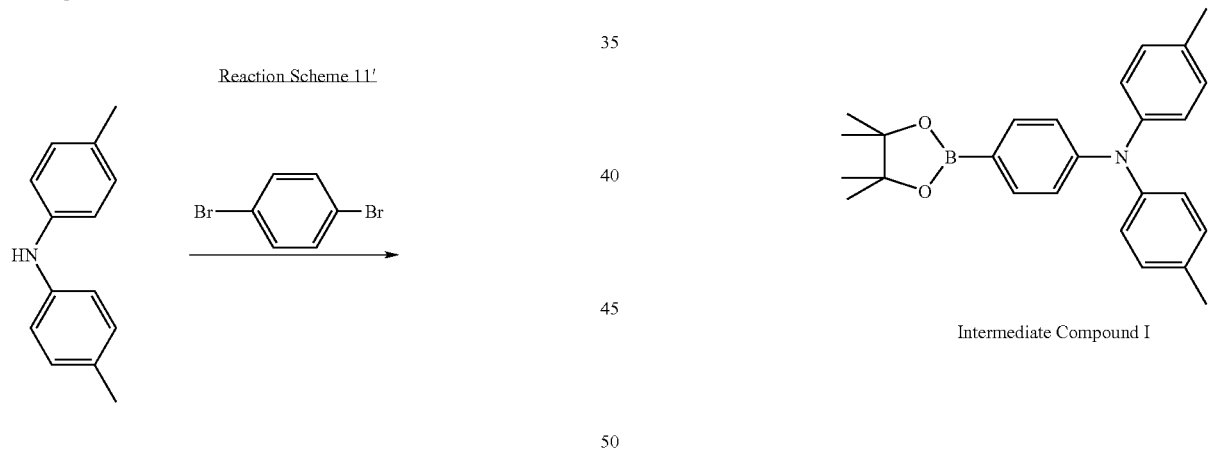

Intermediate Compound J

Intermediate Compound I

Intermediate Compound J was obtained in the same manner as Compound 4 was obtained in Synthesis Example 3 except that ½ equivalent weight of ditolylamine was used instead of N-phenyl-1-naphthylamine and dibromobenzene was used instead of Intermediate B.

Intermediate Compound I was synthesized in the same manner as Intermediate Compound E was prepared through Reaction Scheme 6' in Synthesis Example 5 except that Intermediate Compound J was used instead of Intermediate Compound E'.

Synthesis Example 11
Compound 12 was synthesized through Reaction Scheme 12 below:
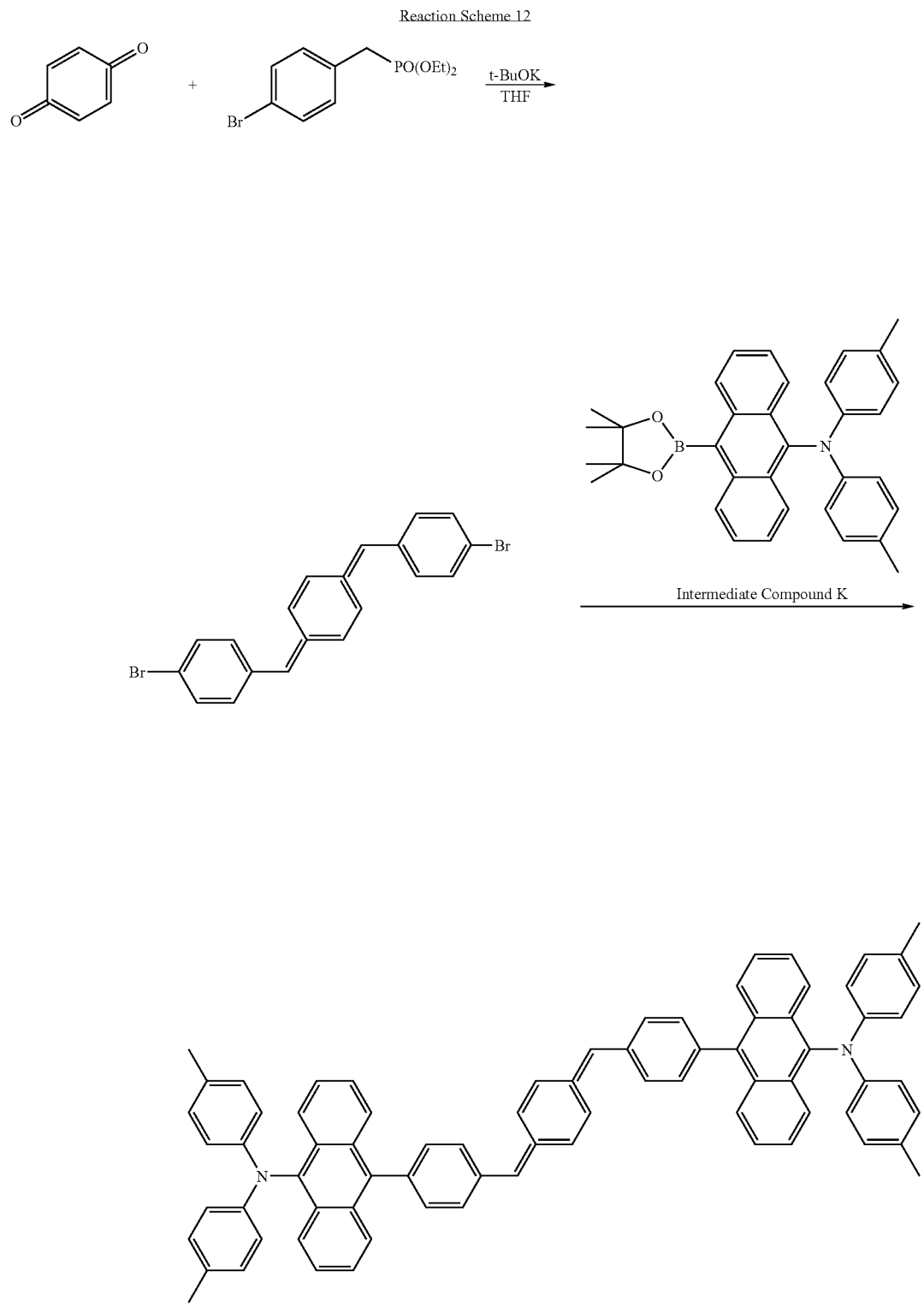
Formula 12

Compound 12 was produced in the same manner as Compound 2 was produced in Synthesis Example 1 except that Intermediate Compound K was used instead of 4-biphenylene boronic acid. Intermediate K was synthesized through Reaction Scheme 12' below:

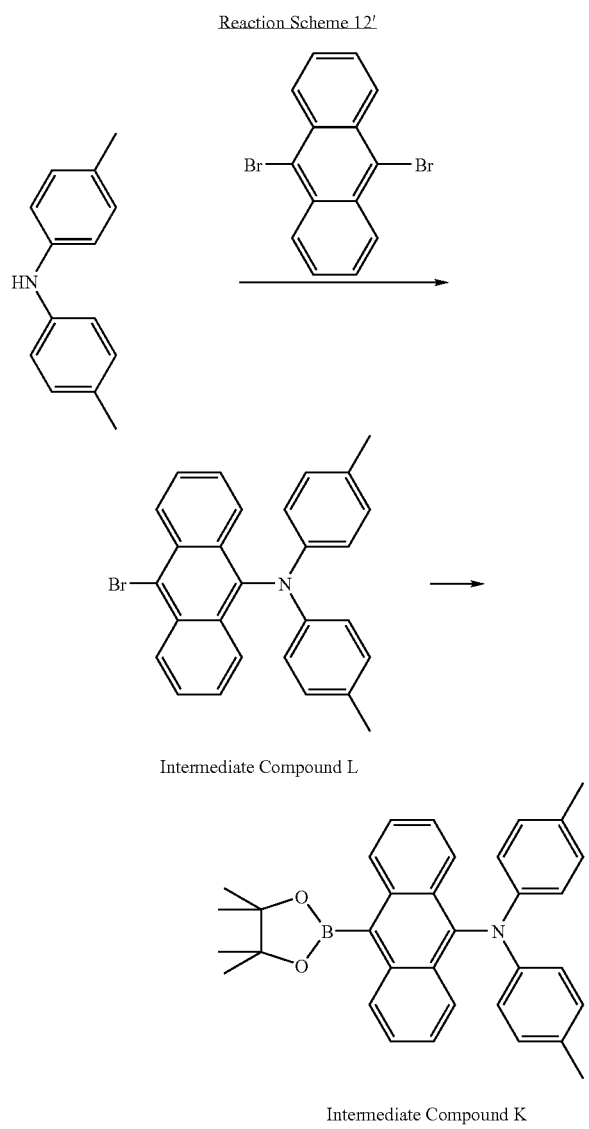

Intermediate Compound L was obtained in the same manner as Compound 4 was obtained in Synthesis Example 3 except that ½ equivalent weight of ditolylamine was used instead of N-phenyl-1-naphthylamine and dibromoanthracene was used instead of Intermediate Compound B.

Intermediate Compound K was synthesized in the same manner as Intermediate Compound E was prepared through Reaction Scheme 6' in Synthesis Example 5 except that Intermediate L was used instead of Intermediate E'.

Measurement Example 1

Thermal Stability Tests for Compounds 2 Through 6 and 9

Thermal stability tests for Compounds 2 through 6 and 9 were carried out by measuring the glass transition temperature (Tg) and the melting point (Tm) of the respective compounds. Tg and Tm were measured by performing thermal analysis using thermo gravimetric analysis (TGA) and differential scanning calorimetry (DSC). The results are shown in Table 1 below:

TABLE 1

| Compound No. | Tg(° C.) | Tm(° C.) |
|---|---|---|
| 2 | 52 | — |
| 3 | 49 | — |
| 4 | 90 | — |
| 5 | — | 319 |
| 6 | — | — |
| 9 | 140 | 352 |

From the results shown in Table 1, it was confirmed that the compounds according to embodiments of the present invention have suitable thermal stability for an organic light emitting device.

Measurement Example 2

Luminance Tests for Compounds 2 Through 6

Figure 2:
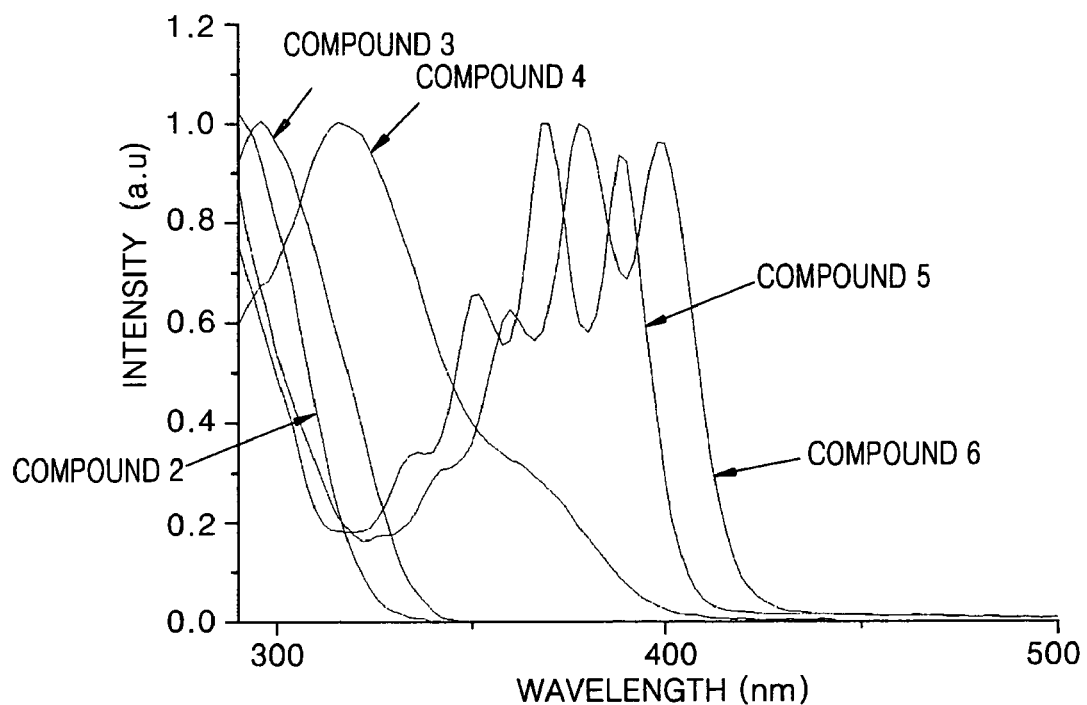
FIG. 2 illustrates absorption spectra of dimethylenecyclohexane compounds according to embodiments of the present invention.
Figure 3:
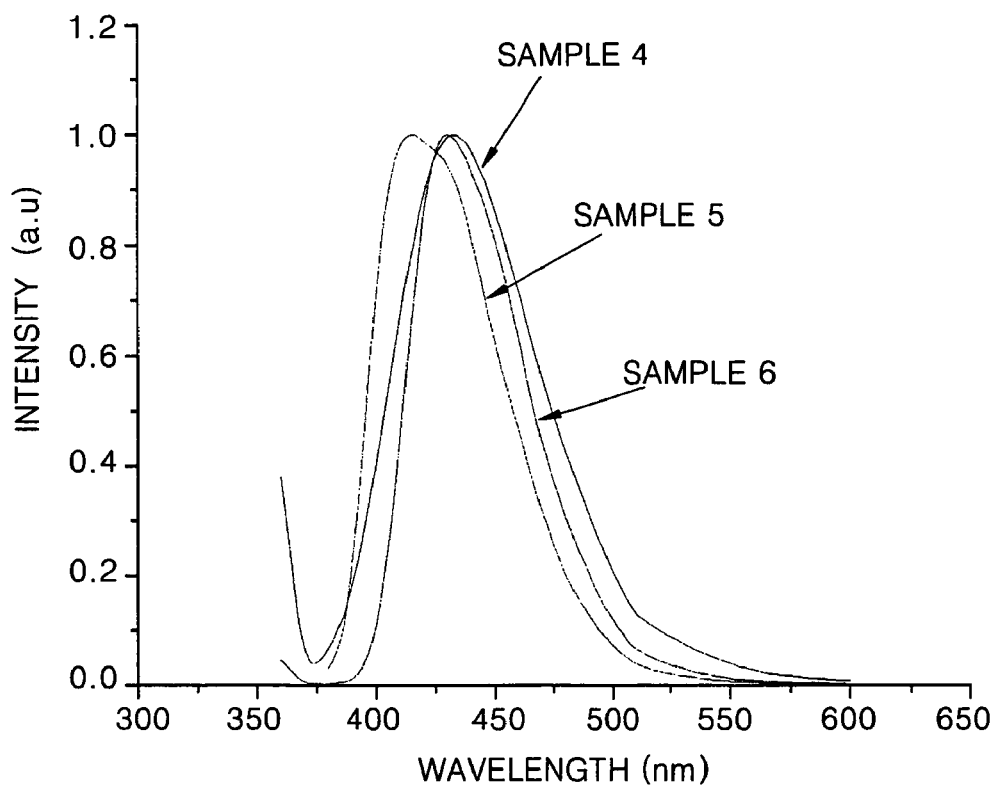
FIG. 3 illustrates photoluminescence (PL) spectra of dimethylenecyclohexane compounds according to embodiments of the present invention.

The luminous properties of Compounds 2 through 6 were measured using UV absorption spectra and photoluminescence (PL) spectra. First, the UV absorption spectrum of 0.2 mM Compound 2 diluted in toluene was obtained using a Shimadzu UV-350 Spectrometer. This process was also performed on Compounds 3 through 6, respectively. In addition, the PL spectrum of 10 mM Compound 2 diluted in toluene was obtained using an ISC PC1 spectrofluorometer having a Xenon lamp. This process was also performed on Compounds 3 through 6, respectively. The results are shown in Table 2. The absorption spectra of Compounds 2, 3, 4, 5 and 6 are illustrated in FIG. 2 and PL spectra of Compounds 4, 5 and 6 are illustrated in FIG. 3.

TABLE 2

| Compound No. | Maximum absorption wavelength (nm) | Maximum PL wavelength (nm) |
|---|---|---|
| 2 | 290 | — |
| 3 | 295 | — |
| 4 | 315 | 432 |
| 5 | 390 | 415 |
| 6 | 400 | 430 |

From the results shown in Table 2, it was confirmed that Compounds according to embodiments of the present invention have emission properties suitable for an organic light emitting device.

Measurement Example 3

Luminance Tests for Compounds 2 Through 5 and 9 (In Film state)

Films were formed using Compounds 2 through 5 and 9, and the absorption spectra, PL spectra, and quantum yields of these films were measured.

Figure 4:
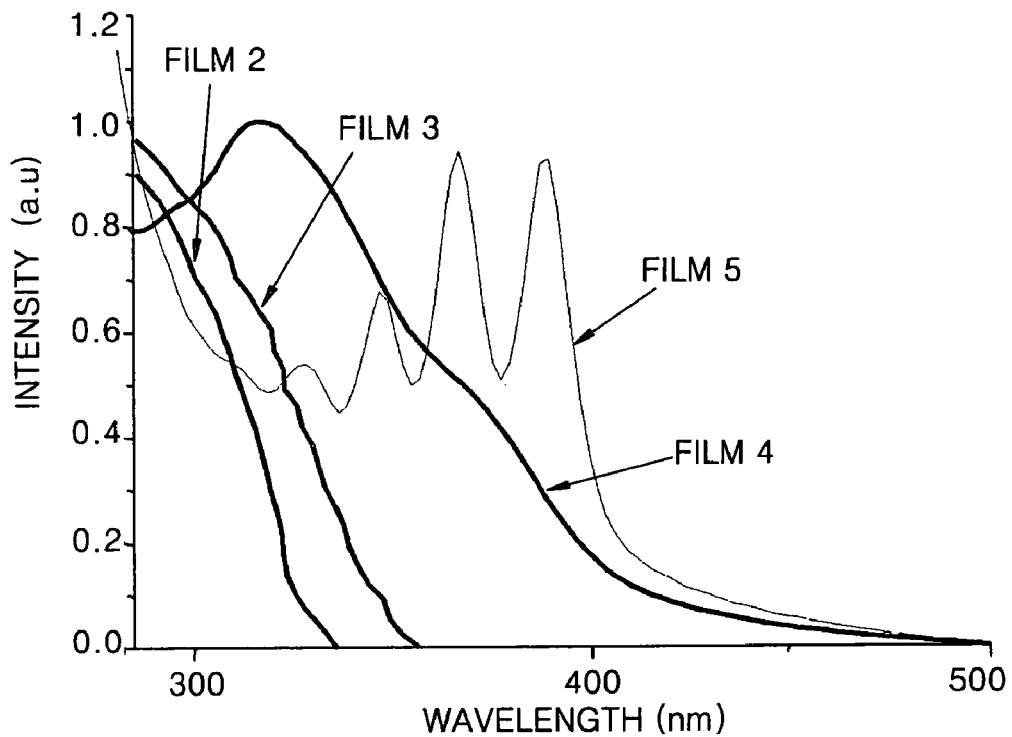
FIG. 4 illustrates absorption spectra of films formed using dimethylenecyclohexane compounds according to embodiments of the present invention.

First, a quartz substrate was washed using chloroform and pure water. Compound 2 was spin coated on the quartz substrate and heat treated at 110° C. for 2 hours to form film with a thickness of 1000 Å. This film is referred to film 2. The absorption spectrum, PL spectrum and quantum yield of film 2 were measured. This process was also performed using Compounds 3 through 5 and 9, respectively, to form films 3 through 5 and 9 and the results are shown in Table 3. The absorption spectra of films 2, 3, 4 and 5 are illustrated in FIG. 4.

TABLE 3

| Film No. | Maximum absorption wavelength (nm) | Maximum PL wavelength (nm) | Quantum Yield (%) |
|---|---|---|---|
| film 2 | 300 | 382 | 16 |
| film 3 | 300 | 358 | 65 |
| film 4 | 320 | 470 | 66 |
| film 5 | 395 | 430 | 23 |
| film 9 | 400 | 440 | — |

From the results shown in Table 3, it was confirmed that films formed of compounds according to embodiments of the present invention had absorption spectra, PL spectra and quantum yields suitable for an organic light emitting device.

Example 1

An organic light emitting device having the following structure was manufactured using compound DPAVBi represented by formula 16 as a dopant of an EML and a compound represented by formula 4 as a host of an EML:

ITO/PEDOT (500 Å)/Compound 4_dopant

DPAVBi (480 Å)/Balq (200 Å)/LiF (10 Å)/Al (2000 Å).

A 15 O/cm² (1000 Å) ITO glass substrate was cut to a size of 50 mm×50 mm×0.7 mm, microwave-washed with acetone isopropyl alcohol for 15 minutes, microwave-washed with pure water for 15 minutes, and washed with UV ozone for 30 minutes. PEDOT-PSS (AI4083) obtained from Bayer Co. was coated on the substrate and heat treated at 110° C. for 5 minutes and heat treated at 200° C. under a nitrogen atmosphere for 5 minutes to form a HIL with a thickness of 500 Å. A mixture including 0.1 g of Compound 4 and 0.05 g of the dopant DPAVBi (5 parts by weight of compound represented by formula 16 based on 100 parts by weight of Compound 4) was spin coated on the HIL and heat treated at 110° C. for 30 minutes to form an EML with a thickness of 480 Å. Then, a Balq compound was vacuum deposited on the EML to form an ETL with a thickness of 200 Å. LiF was vacuum deposited on the ETL to form an EIL with a thickness of 10 Å, and then Al was vacuum deposited on the EIL to form a cathode with a thickness of 2000 Å. As a result, an organic light emitting device illustrated in FIG. 1A was manufactured. The organic light emitting device will be referred to as Sample 1.

Example 2

An organic light emitting device having an ITO/PEDOT (500 Å)/Compound 5_dopant DPAVBi (480 Å)/Balq (200 Å)/LiF (10 Å)/Al (2000 Å) structure was manufactured in the same manner as in Example 1 except that Compound 5 was used instead of Compound 4 as a host. This organic light emitting device will be referred to as Sample 2.

Example 3

An organic light emitting device having an ITO/PEDOT (500 Å)/Compound 4 (480 Å)/Balq (200 Å)/LiF (10 Å)/Al (2000 Å) structure was manufactured in the same manner as in Example 1 except that Compound 4 was used by itself without the use of DPAVBi as a dopant to form the EML. This organic light emitting device will be referred to as Sample 3.

Example 4

An organic light emitting device having an ITO/PEDOT (500 Å)/PVK_Compound 4 (480 Å)/Balq (200 Å)/LiF (10 Å)/Al (2000 Å) structure was manufactured in the same manner as in Example 1 except that 0.01 g of Compound 4 as a dopant and 0.1 g of PVK as a host (10 parts by weight of Compound 4 based on 100 parts by weight of PVK) were used instead of DPAVBi as a dopant and Compound 4 as a host to form the EML. This organic light emitting device will be referred to as Sample 4.

Measurement Example 4

Characteristics of Samples 1, 2, 3 and 4

Figure 5:
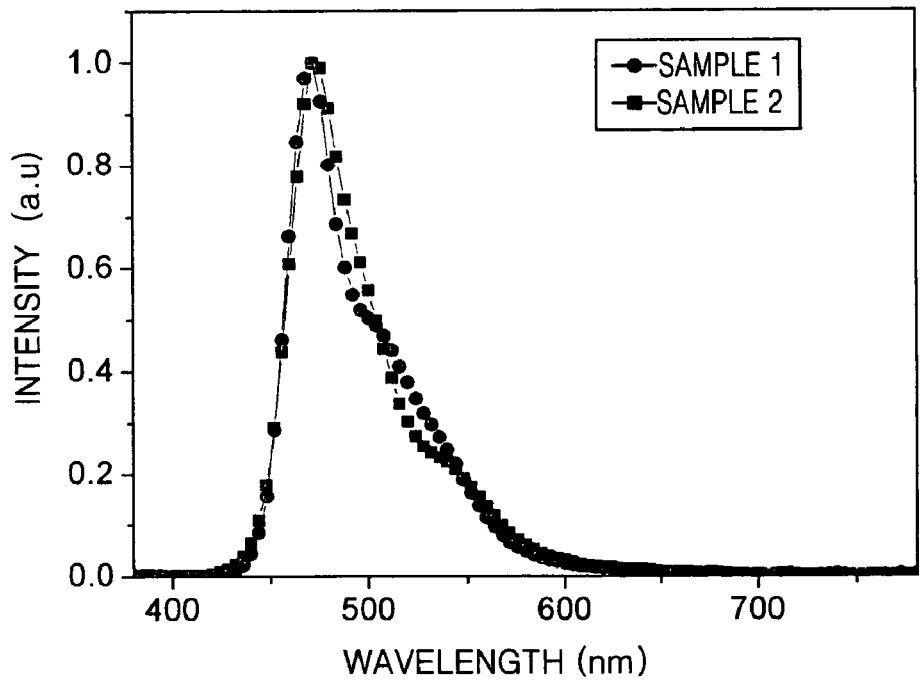
FIG. 5 illustrates luminous intensities of organic light emitting devices including dimethylenecyclohexane compounds according to embodiments of the present invention.

Driving voltages, color purities and efficiencies of Samples 1, 2, 3 and 4 were measured using a PR650 (Spectroscan) Source Measurement Unit. The luminous intensities of Samples 1 and 2 are shown in FIG. 5.

TABLE 5

| Sample No. | Turn on Voltage (V) | CIE Color Coordinate (~100 cd/m²) | Efficiency at 6.6 V (cd/A) |
|---|---|---|---|
| 1 | 3 | (0.16, 0.27) | 1.59 |
| 2 | 3 | (0.15, 0.28) | 5.7 |
| 3 | 4.2 | (0.18, 0.29) | 1.35 |
| 4 | 4.7 | (0.12, 0.14) | 1.2 |

As shown in Table 5, Samples 1 through 4 according to embodiments of the present invention had excellent electrical characteristics.

A dimethylenecyclohexane compound represented by formula 1 according to the present invention has excellent luminous characteristics and thermal stability. Accordingly, an organic light emitting device using the dimethylenecyclohexane compound according to the present invention exhibits a low driving voltage, excellent color purity and high efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A dimethylenecyclohexane compound represented by formula 1:

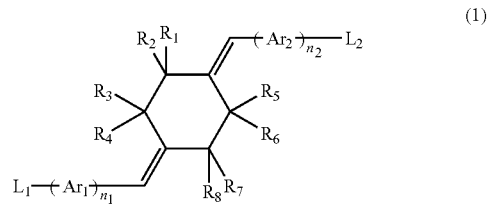

(1)

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z"), and Z' and Z" are each independently a substituted or unsubstituted $C_2$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;

each $Ar_1$ is independently a substituted or unsubstituted $C_6$-$C_{30}$ arylene group, or a substituted or unsubstituted $C_2$-$C_{30}$ heteroarylene group;

each $Ar_2$ is independently a substituted or unsubstituted $C_6$-$C_{30}$ arylene group, or a substituted or unsubstituted $C_2$-$C_{30}$ heteroarylene group;

$n_1$ and $n_2$ are each independently integers from 1 to 5; and $L_1$ and $L_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group having —N(R')(R"), and the R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

2. The dimethylenecyclohexane compound of claim 1, wherein substituents of the substituted alkyl group, the substituted alkoxy group, the substituted arylene group, the substituted heteroarylene group, the substituted aryl group, the substituted heteroaryl group, the substituted cycloalkyl group and the substituted heterocycloalkyl group independently comprise at least one selected from the group consisting of —F; —Cl; —Br; —CN; —NO$_2$; —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_m$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

3. The dimethylenecyclohexane compound of claim 1, wherein $Ar_1$ and $Ar_2$ are each independently selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (α,α-dimethylbenzen)phenylene group, a (N,N'-dimethyl)aminophenylene group, a (N,N'-diphenyl)aminophenylene group, a ($C_1$-$C_{10}$ alkylcyclohexyl)phenylene group, a (anthracenyl)phenylene group, a pentalenylene group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$ alkoxy biphenylenylene group, an anthracenylene group, an azulenylene group, a heptalenylene group, an acenaphthylenylene group, a phenalenylene group, a fluorenylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, and a thianthrenylene group.

4. The dimethylenecyclohexane compound of claim 1, wherein $n_1$ and $n_2$ are each independently 1, 2, or 3.

5. The dimethylenecyclohexane compound of claim 1, wherein $L_1$ and $L_2$ are each independently selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzen)phenyl group, a (N,N'-dimethyl) aminophenyl group, a (N,N'-diphenyl)aminophenyl group, a ($C_1$-$C_{10}$ alkylcyclohexyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthracenyl group, $C_1$-$C_{10}$ alkyl anthracenyl group, a $C_1$-$C_{10}$ alkoxy anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_{1-10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, a $C_1$-$C_{10}$ alkylcyclohexyl group, a $C_1$-$C_{10}$ alkoxycyclohexyl group, an oxiranyl group, a pyrrolidinyl group, a pyrazolidinyl group, an imidazolidinyl group, a piperidinyl group, a piperazinyl group, a morpholinyl group and an amino group having —N(R')(R"); and R' and R" are each independently selected from the group consisting of a hydrogen, a phenyl group, a $C_1$-$C_{10}$ alkyl phenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzen)phenyl group, a (N,N'-dimethyl)aminophenyl group, a (N,N'-diphenyl) aminophenyl group, a ($C_1$-$C_{10}$ alkylcyclohexyl)

phenyl group, an (anthracenyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group and a $C_1$-$C_{10}$ alkyl biphenylenyl.

6. The dimethylenecyclohexane compound of claim 1, wherein $Ar_1$ and $Ar_2$ are identical.

7. The dimethylenecyclohexane compound of claim 1, represented by one of formulae 2 through 15:

(2)

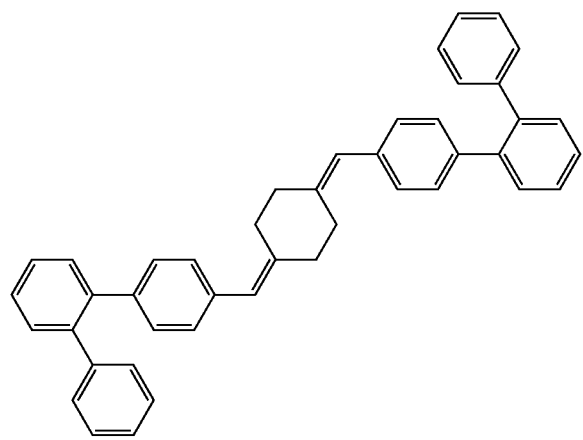

(3)

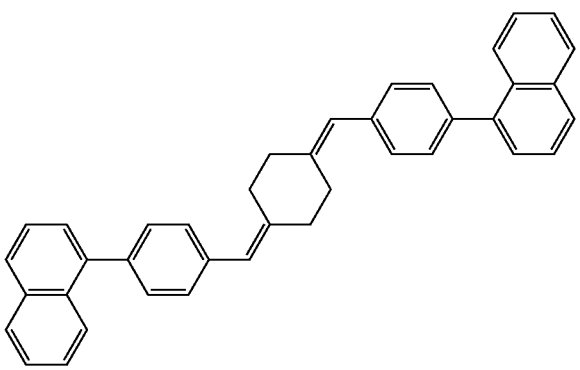

(4)

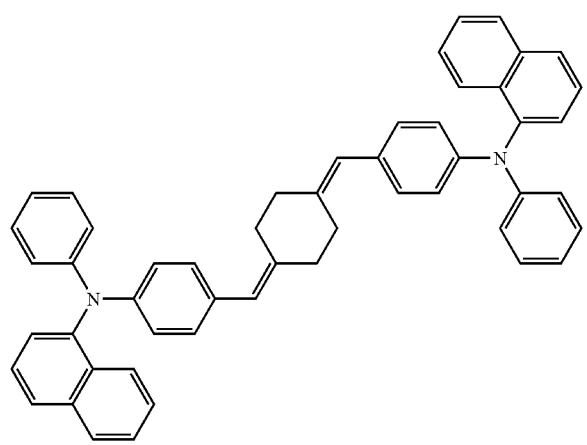

(5)

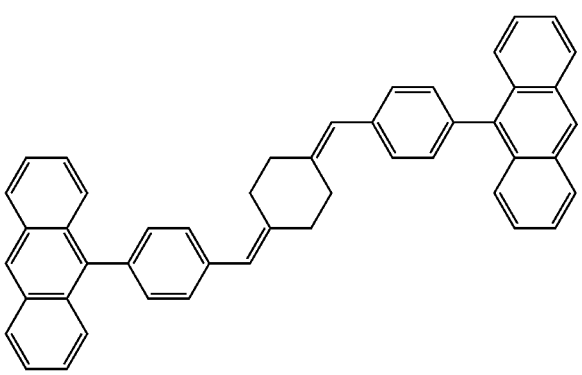

(6)

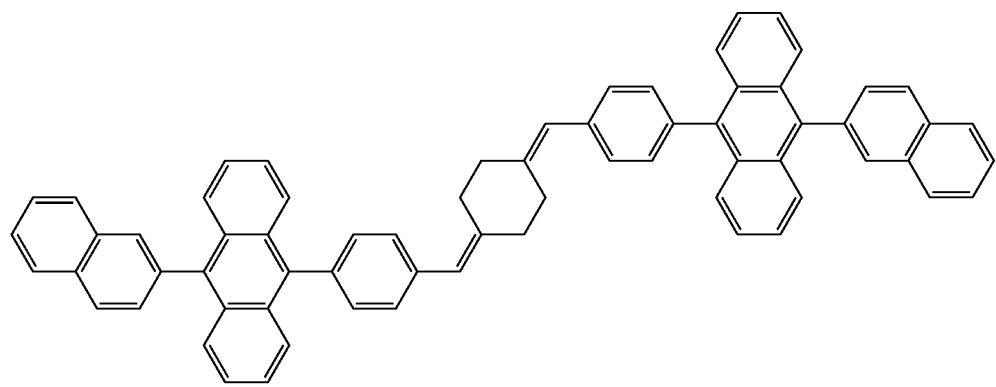

-continued
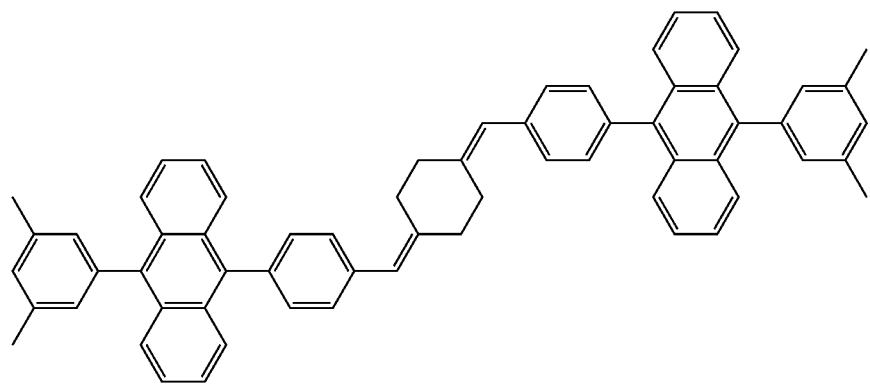
(7)
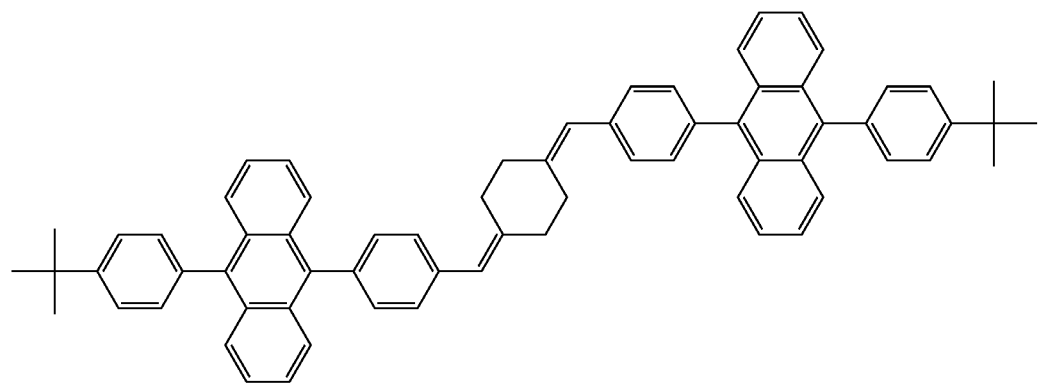
(8)
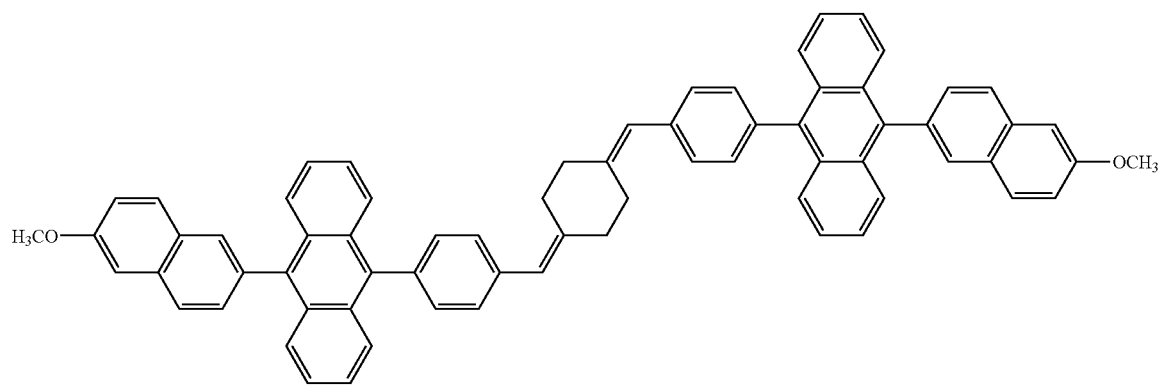
(9)
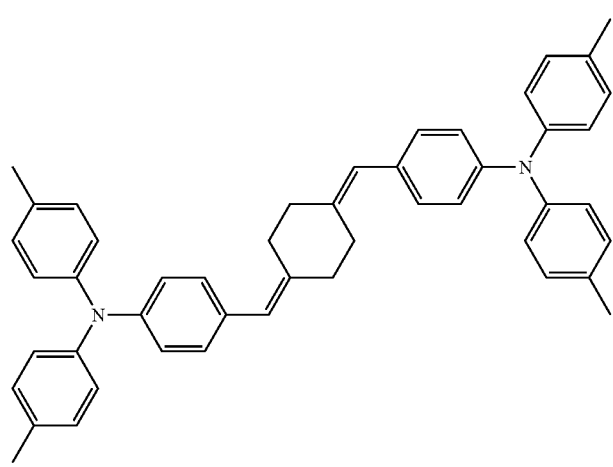
(10)

(11)
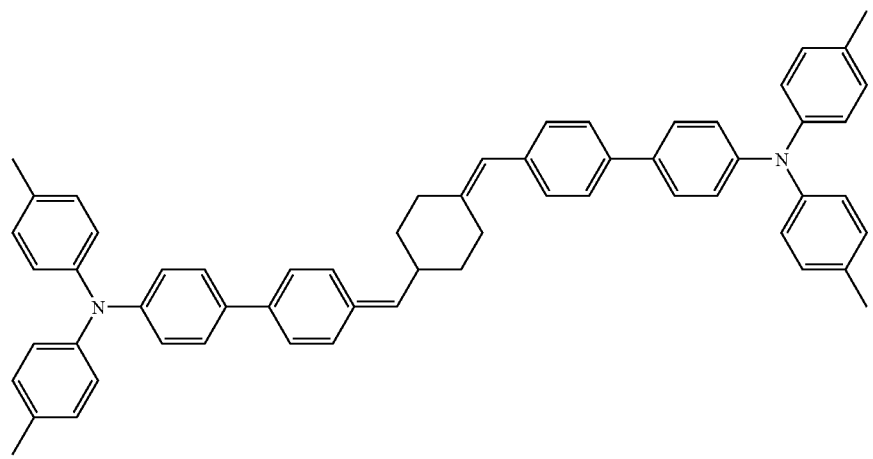
(12)
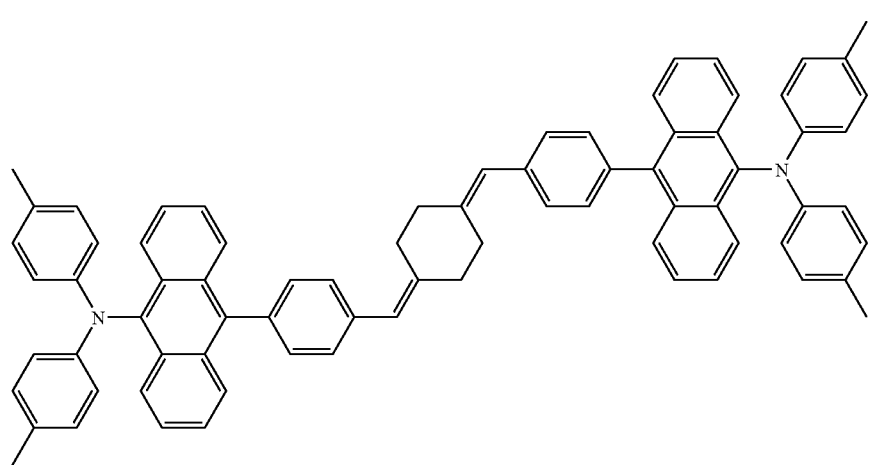
(13)
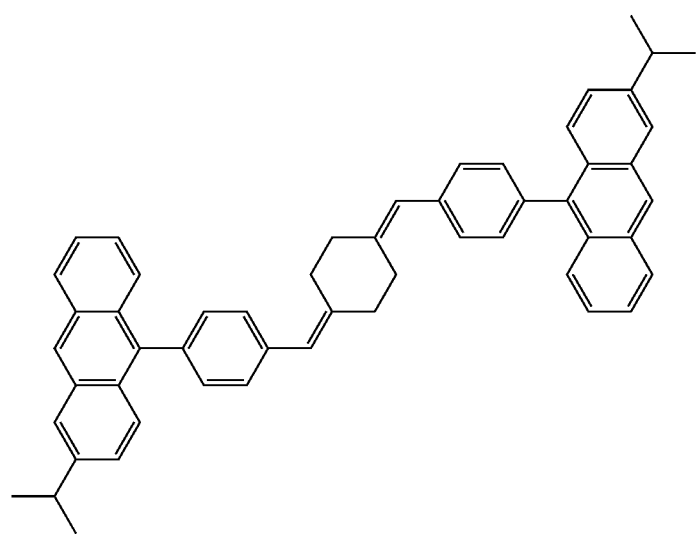

(14)

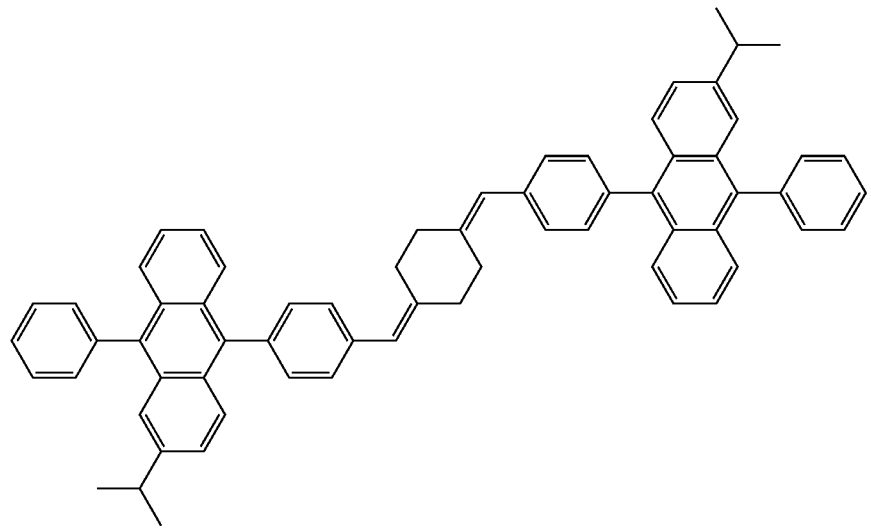

(15)

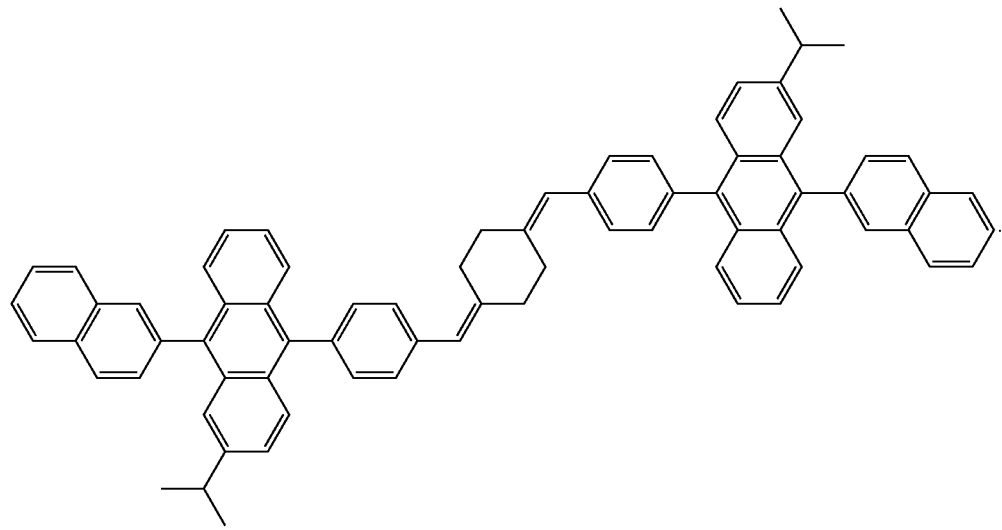

8. An organic light emitting device comprising a first electrode, a second electrode, and at least one organic layer interposed between the first electrode and the second electrode, said at least one organic layer comprising an organic layer comprised of a dimethylenecyclohexane compound of claim 1.

9. A method of preparing the dimethylenecyclohexane compound represented by formula 1, the method comprising:

reacting compounds represented by formula 1a with compounds represented by formulae 1b and 1c to obtain a compound represented by formula 1d; and reacting the compound represented by formula 1d with compounds represented by compounds represented by formulae $L_1$-$Q_1$ and $L_2$-$Q_2$ to obtain the compound represented by formula 1:

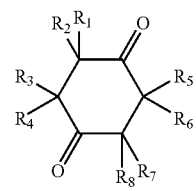
(1a)

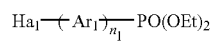
(1b)

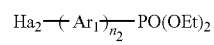
(1c)

-continued (1d)

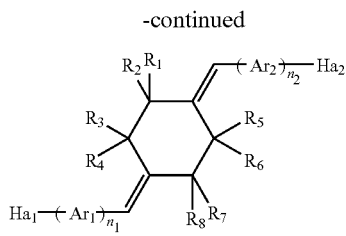

(1)

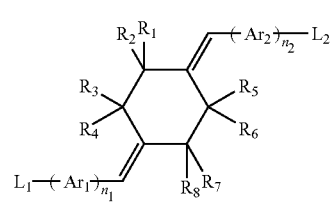

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z"), and Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group;

each $Ar_1$ is independently a substituted or unsubstituted $C_6$-$C_{30}$ arylene group, or a substituted or unsubstituted $C_2$-$C_{30}$ heteroarylene group;

each $Ar_2$ is independently a substituted or unsubstituted $C_6$-$C_{30}$ arylene group, or a substituted or unsubstituted $C_2$-$C_{30}$ heteroarylene group;

$n_1$ and $n_2$ are each independently integers from 1 to 5;

$L_1$ and $L_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group having —N(R')(R"), and R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group;

$Ha_1$ and $Ha_2$ are each independently halogen atoms; and $Q_1$ and $Q_2$ are each independently B-containing groups or H when $L_1$ and $L_2$ are substituted amino groups having —N(R')(R").

10. The method of claim 9, wherein $Q_1$ and $Q_2$ are each independently

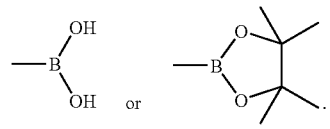

11. The method of claim 9, wherein $Ar_1$ and $Ar_2$ are identical, $n_1$ and $n_2$ are identical, $Ha_1$ and $Ha_2$ are identical and $L_1$ and $L_2$ are identical.

12. The method of claim 9, wherein the dimethylenecyclohexane compound is represented by one of formulae 2 through 15:

(2)

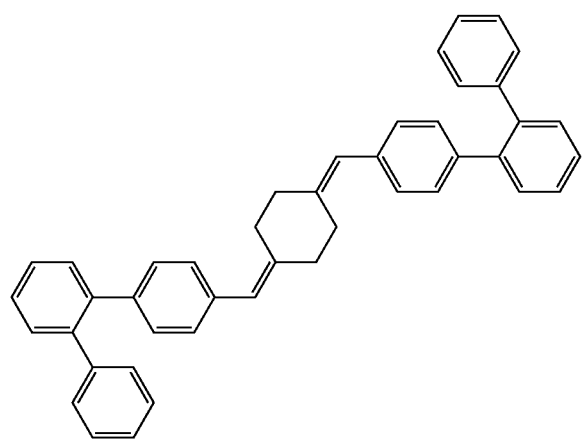

(3)

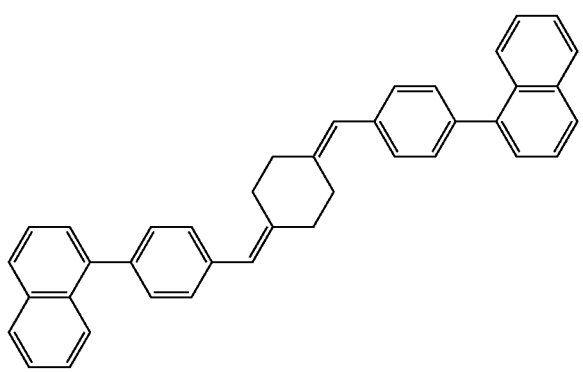

-continued
(4)
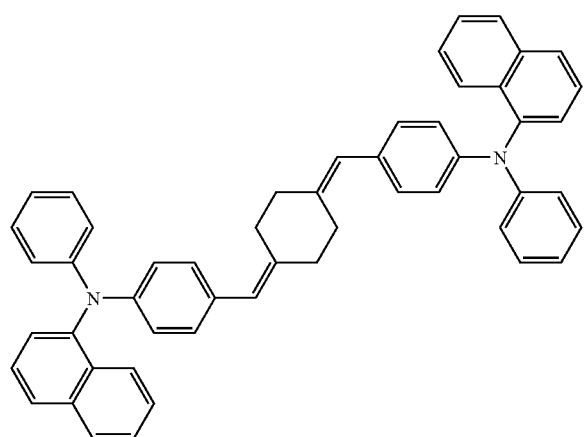
(5)
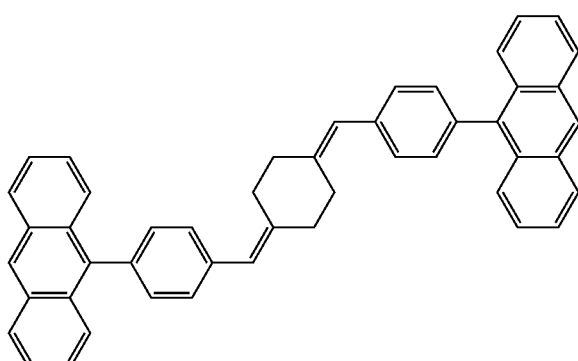
(6)
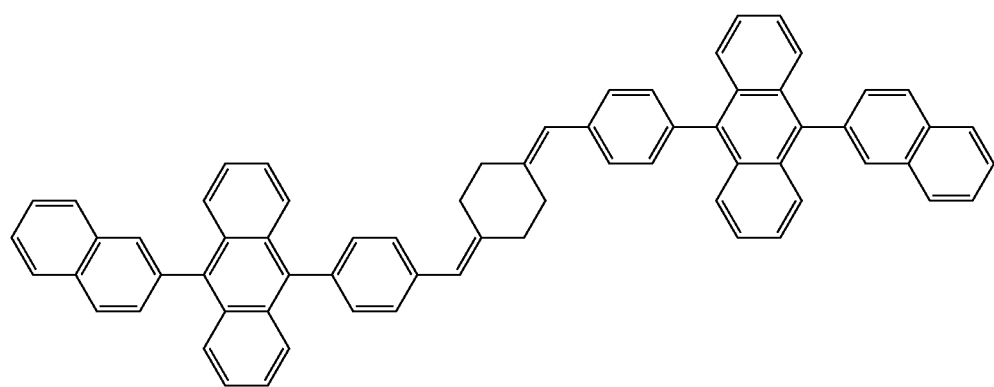
(7)
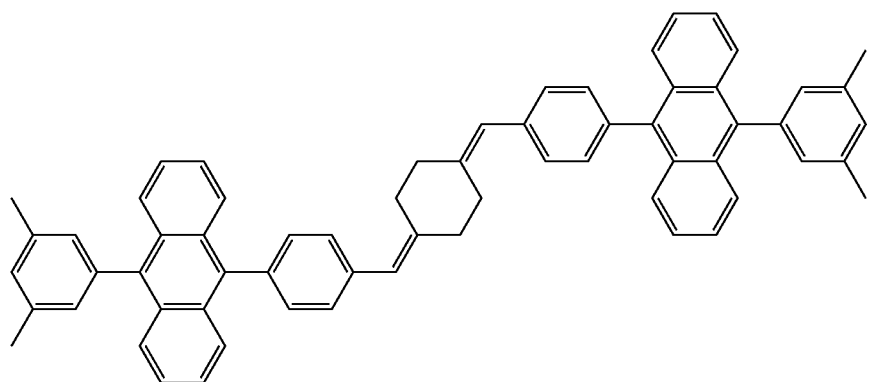
(8)
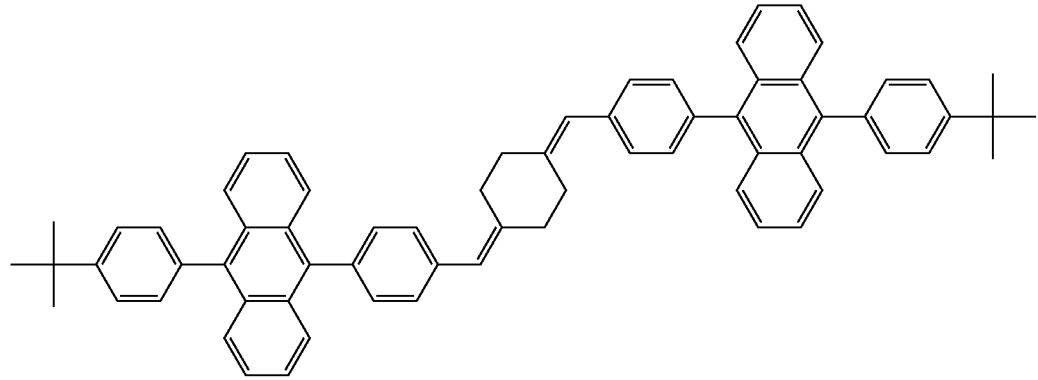

(9)
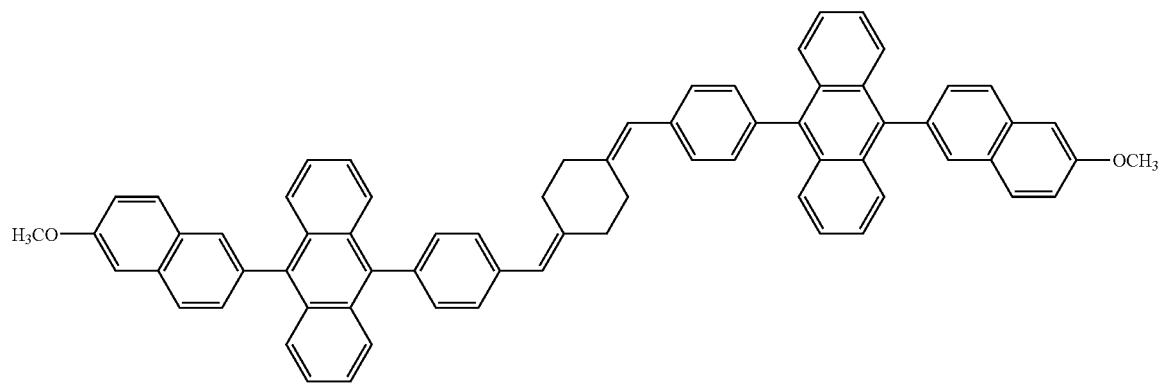
(10)
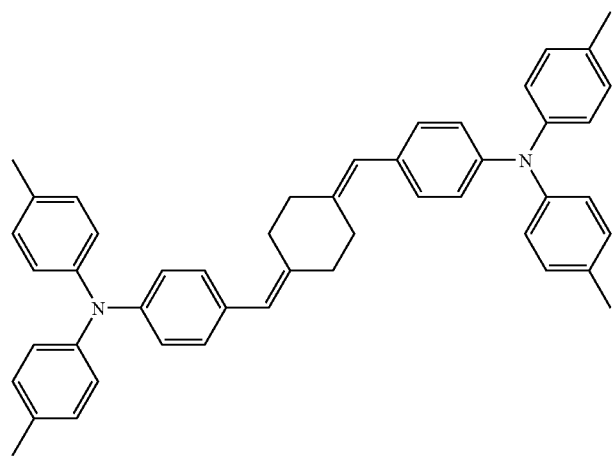
(11)
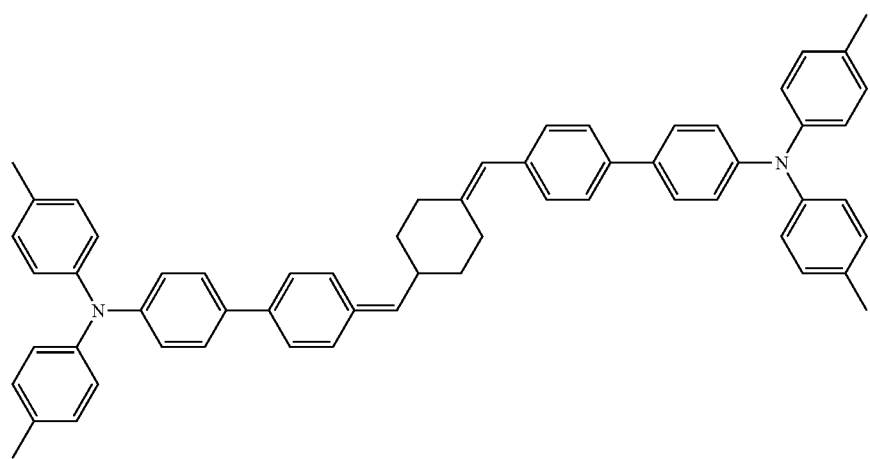

-continued
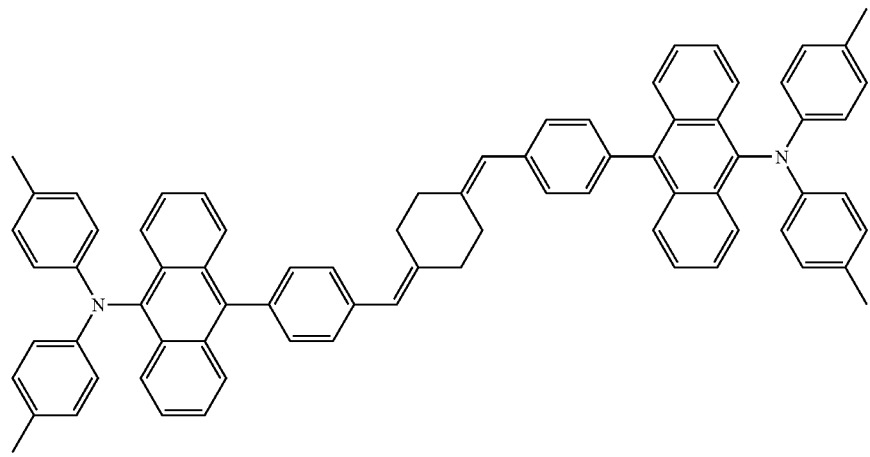
(12)
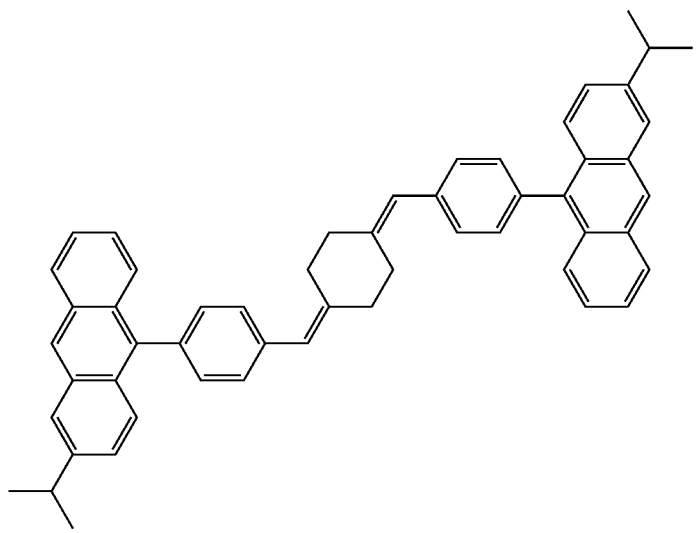
(13)
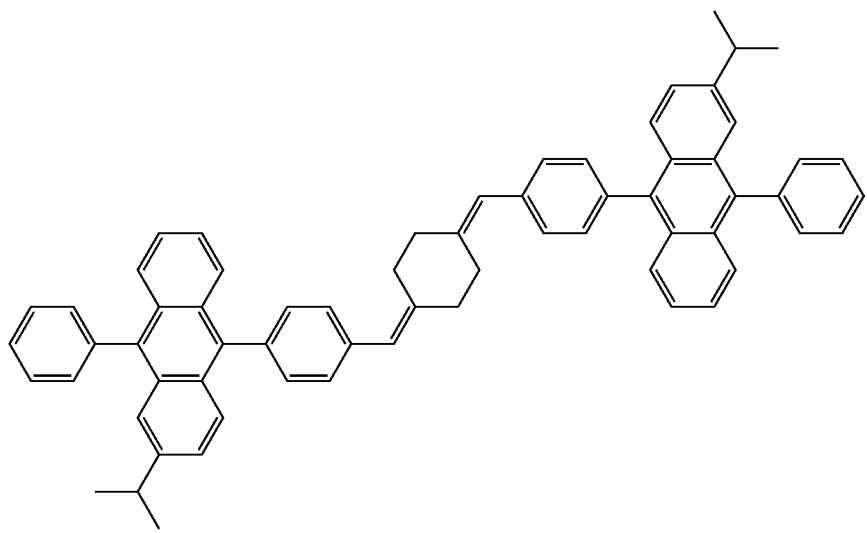
(14)

-continued (15)

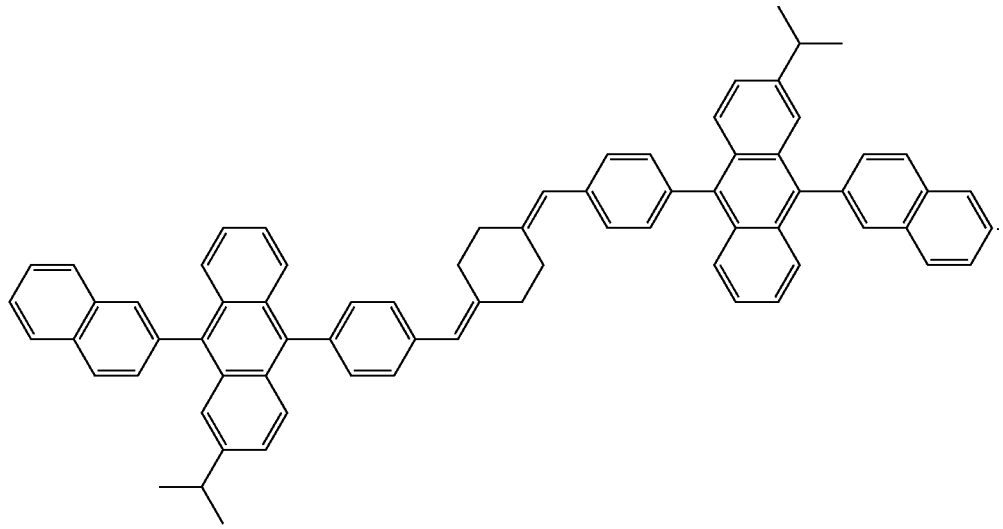

13. An organic light emitting device, comprising:
a first electrode;
a second electrode; and
at least one organic layer interposed between the first electrode and the second electrode, said at least one organic layer comprising a layer comprised of a dimethylenecyclohexane compound represented by Formula 1:

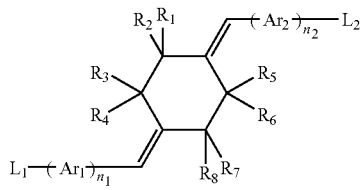

(1)

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z"), and Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;
each $Ar_1$ is independently a substituted or unsubstituted $C_6$-$C_{30}$ arylene group, or a substituted or unsubstituted $C_2$-$C_{30}$ heteroarylene group;
each $Ar_2$ is independently a substituted or unsubstituted $C_6$-$C_{30}$ arylene group, or a substituted or unsubstituted $C_2$-$C_{30}$ heteroarylene group;
$n_1$ and $n_2$ are each independently integers from 1 to 5; and
$L_1$ and $L_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group having —N(R')(R"), and the R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

14. The organic light emitting device of claim 13, wherein substituents of the substituted alkyl group, the substituted alkoxy group, the substituted arylene group, the substituted heteroarylene group, the substituted aryl group, the substituted heteroaryl group, the substituted cycloalkyl group and the substituted heterocycloalkyl group independently comprise at least one selected from the group consisting of —F; —Cl; —Br; —CN; —NO$_2$; —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

15. The organic light emitting device of claim 13, wherein An and $Ar_2$ are each independently selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (α,α-dimethylbenzen)phenylene group, a (N,N'-dimethyl)aminophenylene group, a (N,N'-diphenyl)aminophenylene group, a ($C_1$-$C_{10}$ alkylcyclohexyl)phenylene group, a (anthracenyl)phenylene group, a pentalenylene group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$ alkoxy biphenylenylene group, an anthracenylene group, an azulenylene group, a heptalenylene group, an acenaphthylenylene group, a phenalenylene group, a fluorenylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_1$-$C_{10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, and a thianthrenylene group.

16. The organic light emitting device of claim 13, wherein $n_1$ and $n_2$ are each independently 1, 2, or 3.

17. The organic light emitting device of claim 13, wherein $L_1$ and $L_2$ are each independently selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzen)phenyl group, a (N,N'-dimethyl) aminophenyl group, a (N,N'-diphenyl)aminophenyl group, a ($C_1$-$C_{10}$ alkylcyclohexyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthracenyl group, $C_1$-$C_{10}$ alkyl anthracenyl group, a $C_1$-$C_{10}$ alkoxy anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_{1-10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, a $C_1$-$C_{10}$ alkylcyclohexyl group, a $C_1$-$C_{10}$ alkoxycyclohexyl group, an oxiranyl group, a pyrrolidinyl group, a pyrazolidinyl group, an imidazolidinyl group, a piperidinyl group, a piperazinyl group, a morpholinyl group and an amino group having —N(R')(R''); and R' and R'' are each independently selected from the group consisting of a hydrogen, a phenyl group, a $C_1$-$C_{10}$ alkyl phenyl group, a $C_1$-$C_{10}$alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzen)phenyl group, a (N,N'-dimethyl)aminophenyl group, a (N,N'-diphenyl) aminophenyl group, a ($C_1$-$C_{10}$ alkylcyclohexyl) phenyl group, an (anthracenyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group and a $C_1$-$C_{10}$ alkyl biphenylenyl.

18. The organic light emitting device of claim 13, wherein the dimethylenecyclohexane compound is represented by one of formulae 2 through 15:

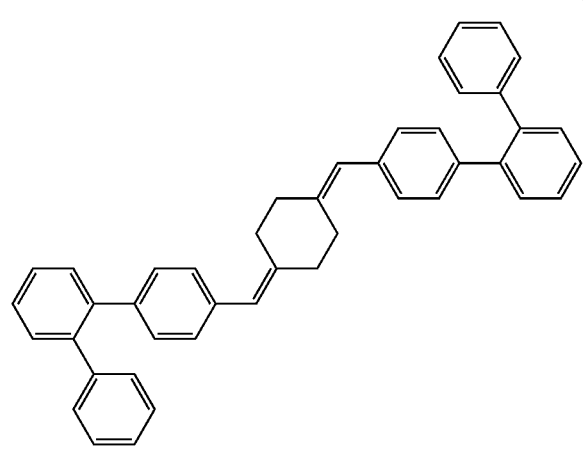

(2)

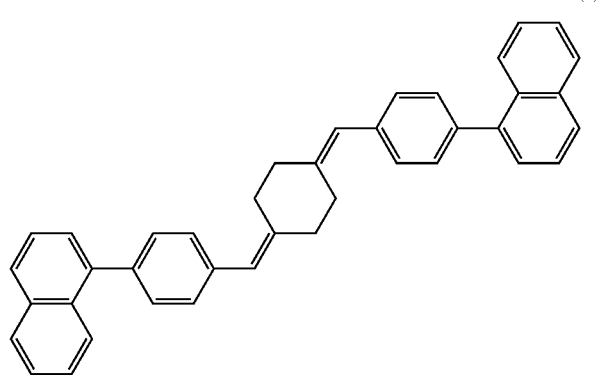

(3)

-continued
(4)
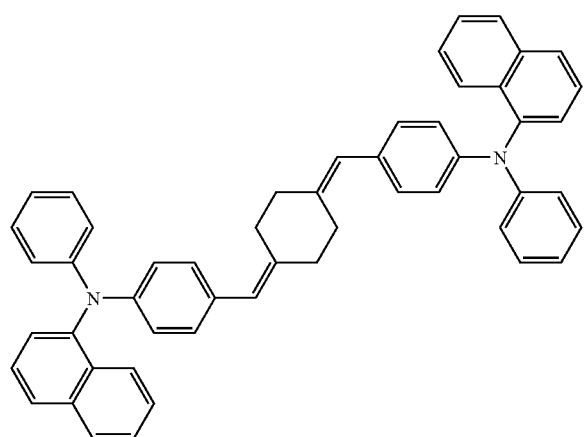
(5)
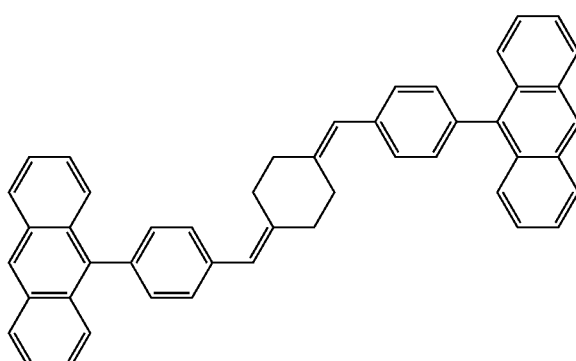
(6)
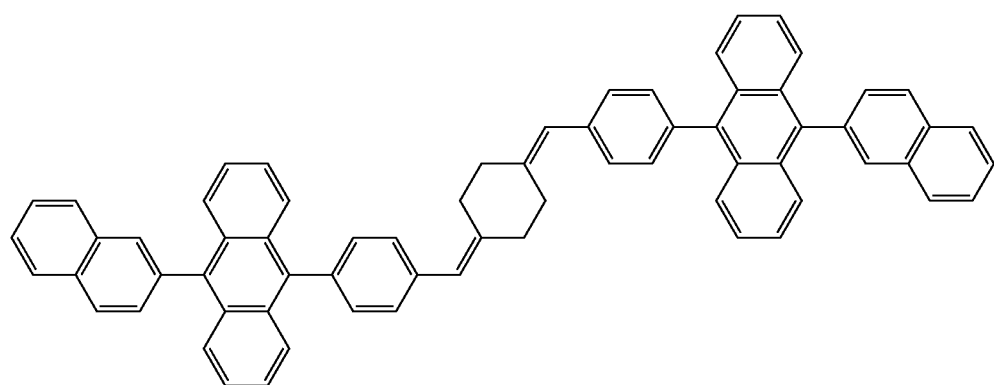
(7)
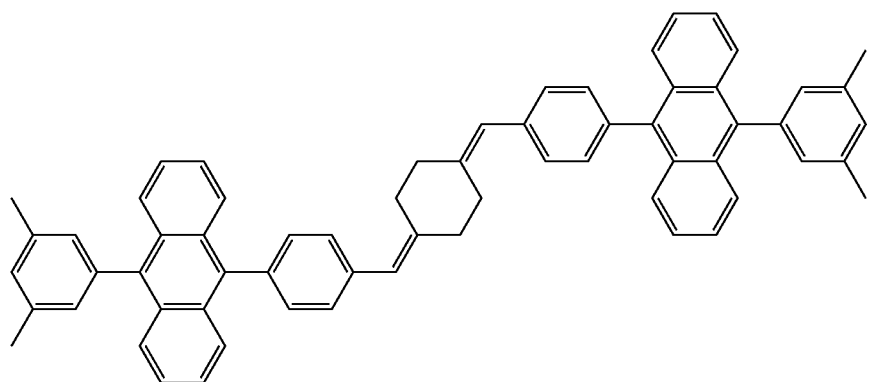
(8)
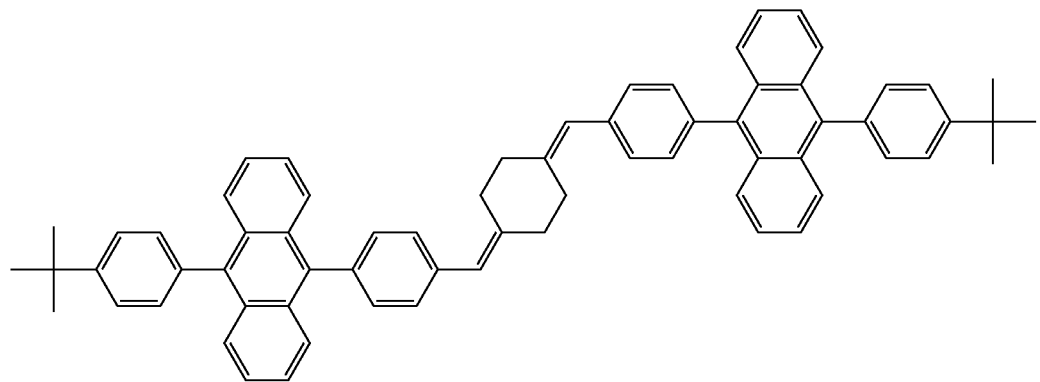

(9)
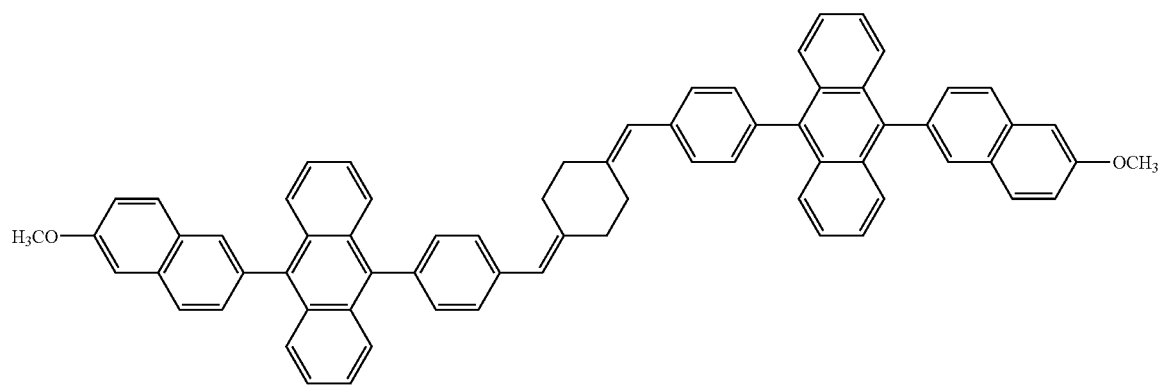
(10)
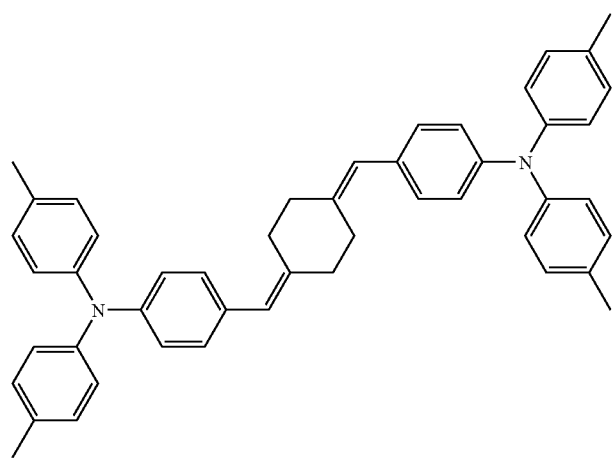
(11)
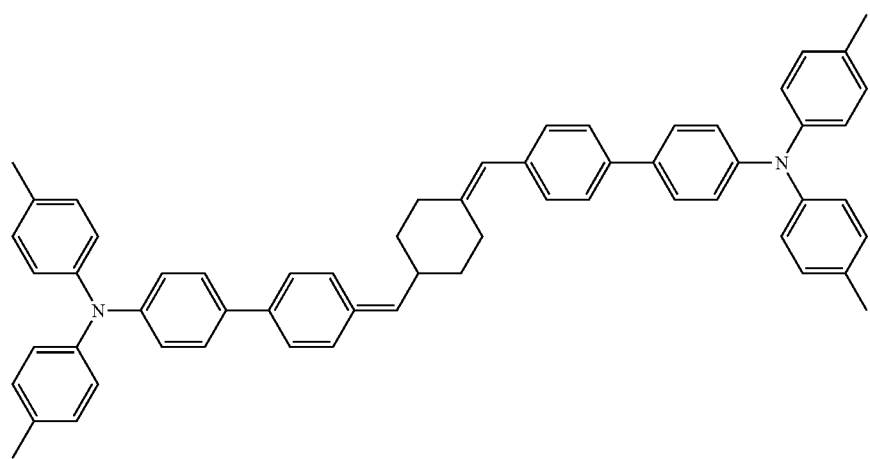

-continued
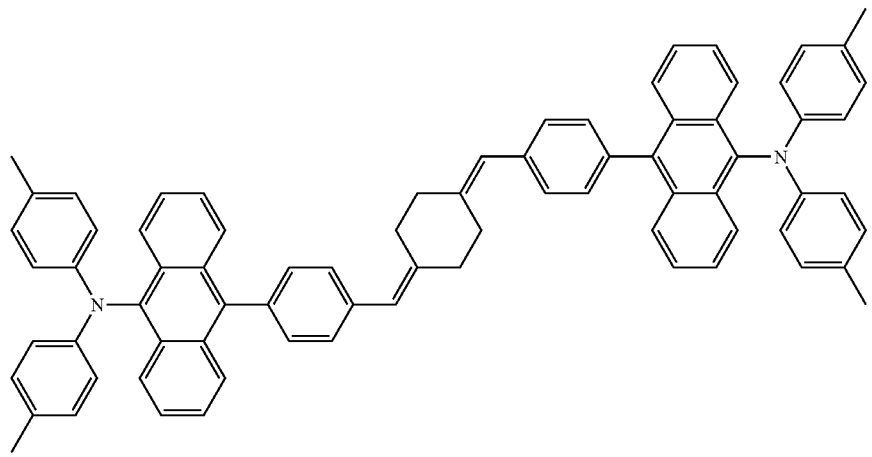
(12)
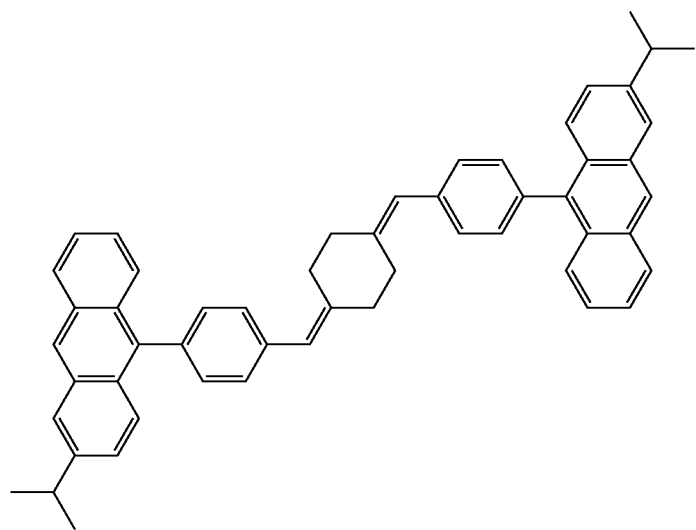
(13)
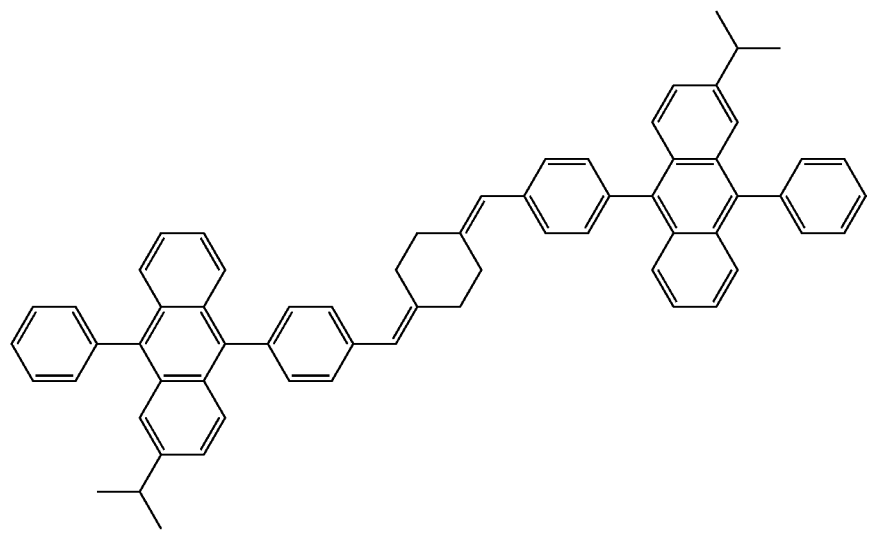
(14)

-continued

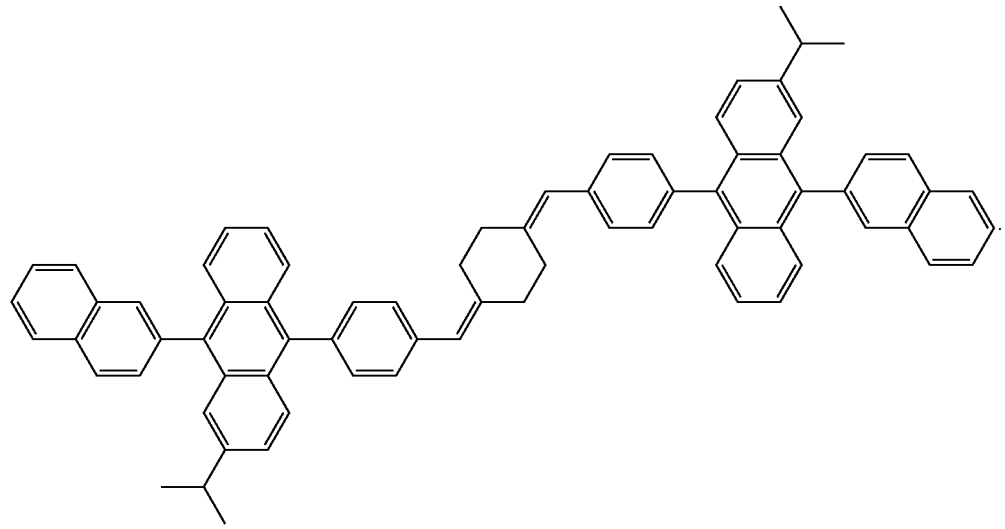

(15)

19. The organic light emitting device of claim 13, wherein said layer comprised of the dimethylenecyclohexane compound represented by Formula 1 comprises at least one selected from the group consisting of a hole injection layer, a hole transport layer, and an emissive layer.

20. The organic light emitting device of claim 13, further comprising at least one layer selected from the group consisting of a hole injection layer, a hole transport layer, an electron blocking layer, a hole blocking layer, an electron transport layer and an electron injection layer between the first electrode and the second electrode.

* * * * *